US011950987B2

(12) United States Patent  
Knittle et al.

(10) Patent No.: US 11,950,987 B2  
(45) Date of Patent: Apr. 9, 2024

(54) MANUFACTURING METHOD FOR INCONTINENCE DETECTION PADS HAVING WIRELESS COMMUNICATION CAPABILITY

(71) Applicant: Hill-Rom Services, Inc., Batesville, IN (US)

(72) Inventors: Brett A. Knittle, Oldenburg, IN (US); Ryan S. Severns, Grand Rapids, MI (US); James D. Voll, Columbus, IN (US); Nicholas Comparone, Batesville, IN (US); Edward J. Koors, Indianapolis, IN (US)

(73) Assignee: Hill-Rom Services, Inc., Batesville, IN (US)

(*) Notice: Subject to any disclaimer, the term of this patent is extended or adjusted under 35 U.S.C. 154(b) by 1022 days.

(21) Appl. No.: 16/856,297

(22) Filed: Apr. 23, 2020

(65) Prior Publication Data

US 2020/0368076 A1 Nov. 26, 2020

Related U.S. Application Data

(60) Provisional application No. 62/940,965, filed on Nov. 27, 2019, provisional application No. 62/850,696, filed on May 21, 2019.

(51) Int. Cl.
 *A61F 13/42* (2006.01)
 *A61F 13/15* (2006.01)
 *G06K 19/07* (2006.01)

(52) U.S. Cl.
 CPC ........ *A61F 13/42* (2013.01); *A61F 13/15723* (2013.01); *A61F 13/15747* (2013.01); 
 (Continued)

(58) Field of Classification Search
 CPC ........ A61F 2013/424; A61F 2013/1591; A61F 13/15747; A61F 13/15723; A61F 13/42; G06K 19/0722
 See application file for complete search history.

(56) References Cited

U.S. PATENT DOCUMENTS

| 1,772,232 A | 8/1930 | Guilder |
| 2,127,538 A | 8/1938 | Seiger |

(Continued)

FOREIGN PATENT DOCUMENTS

| CA | 2361145 A1 | 12/1999 |
| CA | 2494896 A1 | 12/1999 |

(Continued)

OTHER PUBLICATIONS

First Office Action for Chinese Patent Application No. 202010409180.4 dated Aug. 2, 2021 and its English translation (18 pages).

(Continued)

*Primary Examiner* — Vishal I Patel
(74) *Attorney, Agent, or Firm* — Barnes & Thornburg LLP

(57) ABSTRACT

A method of manufacturing incontinence detection pads that have wireless communication capability includes readying an RFID tag applicator to place RFID tags on backsheet material fed between a pair of nip rollers. The backsheet material has a series of electrode traces thereon. The method also includes operating a nip roller motor to feed the backsheet material between the pair of nip rollers and toward the RFID tag applicator, operating the RFID tag applicator to place each RFID tag across regions of a respective electrode trace of the series of electrode traces, and operating RFID tag test equipment to energize each RFID tag a first time and a second time using wireless (Continued)

emissions and receiving return signals from each RFID tag in response to the wireless emissions.

21 Claims, 6 Drawing Sheets

(52) U.S. Cl.
CPC .. *G06K 19/0722* (2013.01); *A61F 2013/1591* (2013.01); *A61F 2013/424* (2013.01)

(56) References Cited

U.S. PATENT DOCUMENTS

| | | | |
|---|---|---|---|
| 2,644,050 A | 6/1953 | Seiger |
| 2,668,202 A | 2/1954 | Kaplan |
| 2,726,294 A | 12/1955 | Kroening et al. |
| 2,907,841 A | 10/1959 | Campbell |
| 3,199,095 A | 8/1965 | Ashida |
| 3,971,371 A | 7/1976 | Bloom |
| 4,069,817 A | 1/1978 | Fenote et al. |
| 4,106,001 A | 8/1978 | Mahoney |
| 4,163,449 A | 8/1979 | Regal |
| 4,191,950 A | 3/1980 | Levin et al. |
| 4,212,295 A | 7/1980 | Snyder |
| 4,228,426 A | 10/1980 | Roberts |
| 4,347,503 A | 8/1982 | Uyehara |
| 4,539,559 A | 9/1985 | Kelley et al. |
| 4,610,745 A | 9/1986 | Sallee et al. |
| 4,747,166 A | 5/1988 | Kuntz |
| 4,965,554 A | 10/1990 | Darling |
| 5,081,422 A | 1/1992 | Shih |
| 5,086,294 A | 2/1992 | Schwab, Jr. |
| 5,137,033 A | 8/1992 | Norton |
| 5,144,284 A | 9/1992 | Hammett |
| 5,291,181 A | 3/1994 | De Ponte |
| 5,438,721 A | 8/1995 | Pahno et al. |
| 5,459,452 A | 10/1995 | DePonte |
| 5,491,609 A | 2/1996 | Dankman et al. |
| 5,537,095 A | 7/1996 | Dick et al. |
| 5,675,854 A | 10/1997 | Zibelin |
| 5,760,694 A | 6/1998 | Nissim et al. |
| 5,790,035 A | 8/1998 | Ho |
| 5,824,883 A | 10/1998 | Park et al. |
| 5,910,080 A | 6/1999 | Selton |
| 5,947,943 A | 9/1999 | Lee |
| 6,028,241 A | 2/2000 | Armstead |
| 6,047,419 A | 4/2000 | Fergusaon |
| 6,104,311 A | 8/2000 | Lastinger |
| 6,292,102 B1 | 9/2001 | Smith |
| 6,340,932 B1 | 1/2002 | Rodgers et al. |
| 6,341,393 B1 | 1/2002 | Votel |
| 6,351,215 B2 | 2/2002 | Rodgers et al. |
| 6,362,737 B1 | 3/2002 | Rodgers et al. |
| 6,384,728 B1 | 5/2002 | Kanor et al. |
| 6,544,200 B1 | 4/2003 | Smith et al. |
| 6,552,661 B1 | 4/2003 | Lastinger et al. |
| 6,583,722 B2 | 6/2003 | Jeutter et al. |
| 6,603,403 B2 | 8/2003 | Jeutter et al. |
| 6,621,410 B1 | 9/2003 | Lastinger et al. |
| 6,639,517 B1 | 10/2003 | Chapman et al. |
| 6,774,800 B2 | 8/2004 | Friedman et al. |
| 6,831,562 B2 | 12/2004 | Rodgers et al. |
| 6,832,507 B1 | 12/2004 | van de Berg et al. |
| 6,876,303 B2 | 4/2005 | Reeder et al. |
| 6,933,849 B2 | 8/2005 | Sawyer |
| 6,948,205 B2 | 9/2005 | Van Der Wurf et al. |
| 6,982,646 B2 | 1/2006 | Rodgers et al. |
| 7,017,213 B2 | 3/2006 | Chisari |
| 7,030,731 B2 | 4/2006 | Lastinger et al. |
| 7,039,997 B2 | 5/2006 | Vogt et al. |
| 7,071,830 B2 | 7/2006 | Sahlberg et al. |
| 7,120,952 B1 | 10/2006 | Bass et al. |
| 7,181,206 B2 | 2/2007 | Pedersen |
| 7,250,547 B1 | 7/2007 | Hofmeister et al. |
| 7,253,729 B2 | 8/2007 | Lastinger et al. |
| 7,274,944 B2 | 9/2007 | Lastinger et al. |
| 7,302,278 B2 | 11/2007 | Lastinger et al. |
| 7,305,246 B2 | 12/2007 | Lastinger et al. |
| 7,308,270 B2 | 12/2007 | Lastinger et al. |
| 7,348,930 B2 | 3/2008 | Lastinger et al. |
| 7,349,701 B2 | 3/2008 | Lastinger et al. |
| 7,355,090 B2 | 4/2008 | Ales, III et al. |
| 7,359,675 B2 | 4/2008 | Lastinger et al. |
| 7,400,860 B2 | 7/2008 | Lastinger et al. |
| 7,424,298 B2 | 9/2008 | Lastinger et al. |
| 7,489,252 B2 | 2/2009 | Long et al. |
| 7,489,282 B2 | 2/2009 | Lastinger et al. |
| 7,498,478 B2 | 3/2009 | Long et al. |
| 7,551,089 B2 | 6/2009 | Sawyer |
| 7,586,385 B2 | 9/2009 | Rokhsaz |
| 7,595,734 B2 | 9/2009 | Long et al. |
| 7,595,756 B2 | 9/2009 | Lastinger et al. |
| 7,598,853 B2 | 10/2009 | Becker et al. |
| 7,598,862 B2 | 10/2009 | Lastinger et al. |
| 7,599,699 B2 | 10/2009 | Lastinger et al. |
| 7,616,959 B2 | 11/2009 | Spenik et al. |
| 7,633,378 B2 | 12/2009 | Rodgers et al. |
| 7,649,125 B2 | 1/2010 | Ales, III et al. |
| 7,663,483 B2 | 2/2010 | Spenik et al. |
| 7,667,600 B2 | 2/2010 | Woodbury et al. |
| 7,812,731 B2 | 10/2010 | Bunza et al. |
| 7,822,386 B2 | 10/2010 | Lastinger et al. |
| 7,834,234 B2 | 11/2010 | Roe et al. |
| 7,834,235 B2 | 11/2010 | Long et al. |
| 7,834,765 B2 | 11/2010 | Sawyer |
| 7,834,766 B2 | 11/2010 | Sawyer |
| 7,838,720 B2 | 11/2010 | Roe et al. |
| 7,849,544 B2 | 12/2010 | Flocard et al. |
| 7,873,319 B2 | 1/2011 | Lastinger et al. |
| 7,977,529 B2 | 7/2011 | Bergman et al. |
| 8,009,646 B2 | 8/2011 | Lastinger et al. |
| 8,073,386 B2 | 12/2011 | Pedersen |
| 8,081,043 B2 | 12/2011 | Rokhsaz |
| 8,102,254 B2 | 1/2012 | Becker et al. |
| 8,104,126 B2 | 1/2012 | Caminade et al. |
| 8,106,782 B2 | 1/2012 | Fredriksson et al. |
| 8,111,165 B2 | 2/2012 | Ortega et al. |
| 8,111,678 B2 | 2/2012 | Lastinger et al. |
| 8,121,856 B2 | 2/2012 | Huster et al. |
| 8,181,290 B2 | 5/2012 | Brykalski et al. |
| 8,191,187 B2 | 6/2012 | Brykalski et al. |
| 8,196,809 B2 | 6/2012 | Thorstensson |
| 8,237,572 B2 | 8/2012 | Clement et al. |
| 8,248,249 B2 | 8/2012 | Clement et al. |
| 8,270,383 B2 | 8/2012 | Lastinger et al. |
| 8,279,069 B2 | 10/2012 | Sawyer |
| 8,319,633 B2 | 11/2012 | Becker et al. |
| 8,325,695 B2 | 12/2012 | Lastinger et al. |
| 8,332,975 B2 | 12/2012 | Brykalski et al. |
| 8,345,651 B2 | 1/2013 | Lastinger et al. |
| 8,395,014 B2 | 3/2013 | Helmer et al. |
| 8,428,039 B2 | 4/2013 | Lastinger et al. |
| 8,428,605 B2 | 4/2013 | Pedersen et al. |
| 8,461,967 B2 | 6/2013 | Partanen et al. |
| 8,461,982 B2 | 6/2013 | Becker et al. |
| 8,482,305 B2 | 7/2013 | Johnson |
| 8,487,774 B2 | 7/2013 | Reeder et al. |
| 8,502,684 B2 | 8/2013 | Bunza et al. |
| 8,628,506 B2 | 1/2014 | Ales, III et al. |
| 8,674,826 B2 | 3/2014 | Becker et al. |
| 8,742,929 B2 | 6/2014 | Sawyer |
| 8,749,319 B2 | 6/2014 | Rokhsaz et al. |
| 8,766,804 B2 | 7/2014 | Reeder et al. |
| 8,842,013 B2 | 9/2014 | Sawyer |
| 8,855,089 B2 | 10/2014 | Lastinger et al. |
| 8,866,615 B2 | 10/2014 | Sawyer |
| 8,878,557 B2 | 11/2014 | Kristiansen et al. |
| 8,878,676 B2 | 11/2014 | Koblasz |
| 8,896,449 B2 | 11/2014 | Sawyer |
| 8,914,923 B2 | 12/2014 | Smith |
| 8,933,292 B2 | 1/2015 | Abraham et al. |
| 8,962,909 B2 | 2/2015 | Groosman et al. |
| 8,978,452 B2 | 3/2015 | Johnson et al. |
| 9,048,819 B2 | 6/2015 | Rokhsaz et al. |

(56) References Cited

U.S. PATENT DOCUMENTS

| | | |
|---|---|---|
| 9,064,140 B2 | 6/2015 | Voutilainen et al. |
| 9,107,776 B2 | 8/2015 | Bergman et al. |
| 9,160,054 B2 | 10/2015 | Yu et al. |
| 9,323,797 B2 | 4/2016 | Acree |
| 9,366,644 B1 | 6/2016 | Lastinger et al. |
| 9,432,132 B2 | 8/2016 | Tuominen |
| 9,506,886 B1 | 11/2016 | Woodbury et al. |
| 9,649,230 B1 | 5/2017 | Li |
| 9,719,951 B1 | 8/2017 | Woodbury et al. |
| 10,022,277 B2 | 7/2018 | Heil et al. |
| 10,159,607 B2 | 12/2018 | Monson et al. |
| 10,500,105 B2 | 12/2019 | Monson et al. |
| 2002/0011932 A1 | 1/2002 | Rodgers et al. |
| 2002/0033757 A1 | 3/2002 | Rodgers et al. |
| 2002/0145525 A1 | 10/2002 | Friedman et al. |
| 2002/0145526 A1 | 10/2002 | Friedman et al. |
| 2003/0030568 A1 | 2/2003 | Lastinger et al. |
| 2005/0003763 A1 | 1/2005 | Lastinger et al. |
| 2005/0003865 A1 | 1/2005 | Lastinger et al. |
| 2005/0046578 A1 | 3/2005 | Pires |
| 2005/0052282 A1 | 3/2005 | Rodgers et al. |
| 2005/0060246 A1 | 3/2005 | Lastinger et al. |
| 2005/0174246 A1 | 8/2005 | Picco et al. |
| 2005/0242946 A1 | 11/2005 | Hubbard, Jr. et al. |
| 2005/0250453 A1 | 11/2005 | Lastinger et al. |
| 2005/0277441 A1 | 12/2005 | Lastinger et al. |
| 2005/0282545 A1 | 12/2005 | Lastinger et al. |
| 2005/0282553 A1 | 12/2005 | Lastinger et al. |
| 2006/0164320 A1 | 7/2006 | Lastinger et al. |
| 2006/0270351 A1 | 11/2006 | Lastinger et al. |
| 2007/0151660 A1 | 7/2007 | Adams et al. |
| 2007/0159332 A1 | 7/2007 | Koblasz |
| 2007/0202809 A1 | 8/2007 | Lastinger et al. |
| 2007/0270774 A1 | 11/2007 | Bergman et al. |
| 2008/0116990 A1 | 5/2008 | Rokhsaz |
| 2008/0204245 A1 | 8/2008 | Blair et al. |
| 2008/0262376 A1 | 10/2008 | Price |
| 2008/0263776 A1 | 10/2008 | O'Reagan et al. |
| 2008/0300559 A1 | 12/2008 | Gustafson et al. |
| 2009/0160648 A1 | 6/2009 | Rokhsaz |
| 2009/0289743 A1 | 11/2009 | Rokhsaz |
| 2009/0292265 A1 | 11/2009 | Helmer et al. |
| 2009/0315728 A1 | 12/2009 | Ales, III et al. |
| 2009/0326417 A1 | 12/2009 | Ales, III et al. |
| 2010/0043143 A1 | 2/2010 | O'Reagan et al. |
| 2011/0025458 A1 | 2/2011 | Rokhsaz et al. |
| 2011/0025473 A1 | 2/2011 | Rokhsaz et al. |
| 2011/0092890 A1 | 4/2011 | Stryker et al. |
| 2011/0115635 A1 | 5/2011 | Petrovski et al. |
| 2011/0263952 A1 | 10/2011 | Bergman et al. |
| 2011/0283459 A1 | 11/2011 | Essers |
| 2011/0291810 A1 | 12/2011 | Rokhsaz et al. |
| 2011/0295619 A1 | 12/2011 | Tough |
| 2011/0300808 A1 | 12/2011 | Rokhsaz et al. |
| 2011/0302720 A1 | 12/2011 | Yakam et al. |
| 2011/0309937 A1 | 12/2011 | Bunza et al. |
| 2012/0092027 A1 | 4/2012 | Forster |
| 2012/0105233 A1 | 5/2012 | Bobey et al. |
| 2012/0119912 A1 | 5/2012 | Ortega et al. |
| 2012/0130330 A1 | 5/2012 | Wilson et al. |
| 2012/0165772 A1 | 6/2012 | Groosman et al. |
| 2012/0216607 A1 | 8/2012 | Sjöholm et al. |
| 2012/0217311 A1 | 8/2012 | Rokhsaz et al. |
| 2012/0268758 A1 | 10/2012 | Lewis et al. |
| 2013/0019405 A1 | 1/2013 | Flanagan et al. |
| 2013/0079590 A1 | 3/2013 | Bengtson |
| 2013/0109929 A1 | 5/2013 | Menzel |
| 2013/0123726 A1 | 5/2013 | Yu et al. |
| 2013/0254141 A1 | 9/2013 | Barda et al. |
| 2014/0120836 A1 | 5/2014 | Rokhsaz et al. |
| 2014/0148772 A1 | 5/2014 | Hu et al. |
| 2014/0152442 A1 | 6/2014 | Li |
| 2014/0200538 A1 | 7/2014 | Euliano et al. |
| 2014/0236629 A1 | 8/2014 | Kim et al. |
| 2014/0244644 A1 | 8/2014 | Mashinchi et al. |
| 2014/0247125 A1 | 9/2014 | Barsky |
| 2014/0266735 A1 | 9/2014 | Riggio et al. |
| 2014/0276504 A1 | 9/2014 | Heil et al. |
| 2014/0296808 A1 | 10/2014 | Curran et al. |
| 2014/0358099 A1 | 12/2014 | Durgin et al. |
| 2015/0080819 A1 | 3/2015 | Charna et al. |
| 2015/0080834 A1 | 3/2015 | Mills |
| 2015/0087935 A1 | 3/2015 | Davis et al. |
| 2016/0267769 A1 | 9/2016 | Rokhsaz et al. |
| 2017/0098044 A1 | 4/2017 | Lai et al. |
| 2017/0246063 A1 | 8/2017 | Monson et al. |
| 2017/0296396 A1 | 10/2017 | Ricciardi et al. |
| 2018/0021184 A1 | 1/2018 | Monson et al. |
| 2018/0325744 A1 | 11/2018 | Weidman et al. |
| 2019/0060137 A1 | 2/2019 | Severns et al. |
| 2019/0091074 A1 | 3/2019 | Monson et al. |
| 2019/0117468 A1 | 4/2019 | Toong |
| 2019/0262195 A1 | 8/2019 | Glaug et al. |

FOREIGN PATENT DOCUMENTS

| | | |
|---|---|---|
| CN | 102568259 A | 7/2012 |
| CN | 202711437 U | 1/2013 |
| CN | 102985853 A | 3/2013 |
| DE | 4137631 A1 | 5/1992 |
| DE | 69906388 T2 | 2/2004 |
| DE | 69915370 T2 | 3/2005 |
| DE | 69917491 T2 | 5/2005 |
| DE | 60016946 T2 | 6/2006 |
| DE | 102007050074 A1 | 4/2009 |
| EP | 0335279 A1 | 10/1989 |
| EP | 1153317 B1 | 3/2003 |
| EP | 1147603 B1 | 3/2004 |
| EP | 1149305 B1 | 5/2004 |
| EP | 1218771 B1 | 12/2004 |
| EP | 1286179 B1 | 11/2005 |
| EP | 1868553 A1 | 12/2007 |
| EP | 2014267 A1 | 1/2009 |
| EP | 1410353 B1 | 12/2009 |
| EP | 1897278 B1 | 1/2010 |
| EP | 1684615 B1 | 2/2010 |
| EP | 2313044 A2 | 4/2011 |
| EP | 1959900 B1 | 2/2012 |
| EP | 2452183 A1 | 5/2012 |
| EP | 1994650 B1 | 12/2012 |
| EP | 2579069 A2 | 4/2013 |
| EP | 2542200 B1 | 2/2014 |
| EP | 2444039 B1 | 5/2014 |
| EP | 2729107 A1 | 5/2014 |
| EP | 2738748 A1 | 6/2014 |
| EP | 2156222 B1 | 8/2015 |
| EP | 2496197 B1 | 8/2015 |
| EP | 2019659 B1 | 4/2016 |
| EP | 2582341 B1 | 4/2016 |
| EP | 2739254 B1 | 11/2016 |
| EP | 3451235 A1 | 3/2019 |
| GB | 145859 | 3/1919 |
| GB | 2145859 | 5/1924 |
| GB | 2408204 A | 11/2003 |
| WO | WO 89/10110 A1 | 4/1989 |
| WO | WO 94/20002 A1 | 3/1994 |
| WO | WO 00/44091 A2 | 7/2000 |
| WO | WO 01/25817 A2 | 4/2001 |
| WO | WO 02/103645 A2 | 12/2002 |
| WO | WO 2006/108540 A1 | 10/2006 |
| WO | WO 2007/069968 A1 | 6/2007 |
| WO | WO 2008/130298 A1 | 10/2008 |
| WO | WO 2010/001271 A2 | 1/2010 |
| WO | WO 2010/043368 A1 | 4/2010 |
| WO | WO 2011/107580 A1 | 9/2011 |
| WO | WO 2012/136157 A1 | 10/2012 |
| WO | WO 2014/165041 A2 | 10/2014 |
| WO | WO 2015/137999 A1 | 9/2015 |

(56) References Cited

FOREIGN PATENT DOCUMENTS

WO        2017087452 A1      5/2017
WO     WO-2017087452 A1 *  5/2017    ........... A61B 5/0004

OTHER PUBLICATIONS

European Search Report of European Patent Application No. 20173819.2 dated Oct. 16, 2020; 6 pages.
Second Office Action for Chinese Patent Application No. 202010409180.4 dated Dec. 17, 2021 and its English translation (18 pages).
Notice of Refusal for Chinese Patent Application No. 202010409180.4 dated Apr. 1, 2022 and its English translation (16 pages).

* cited by examiner

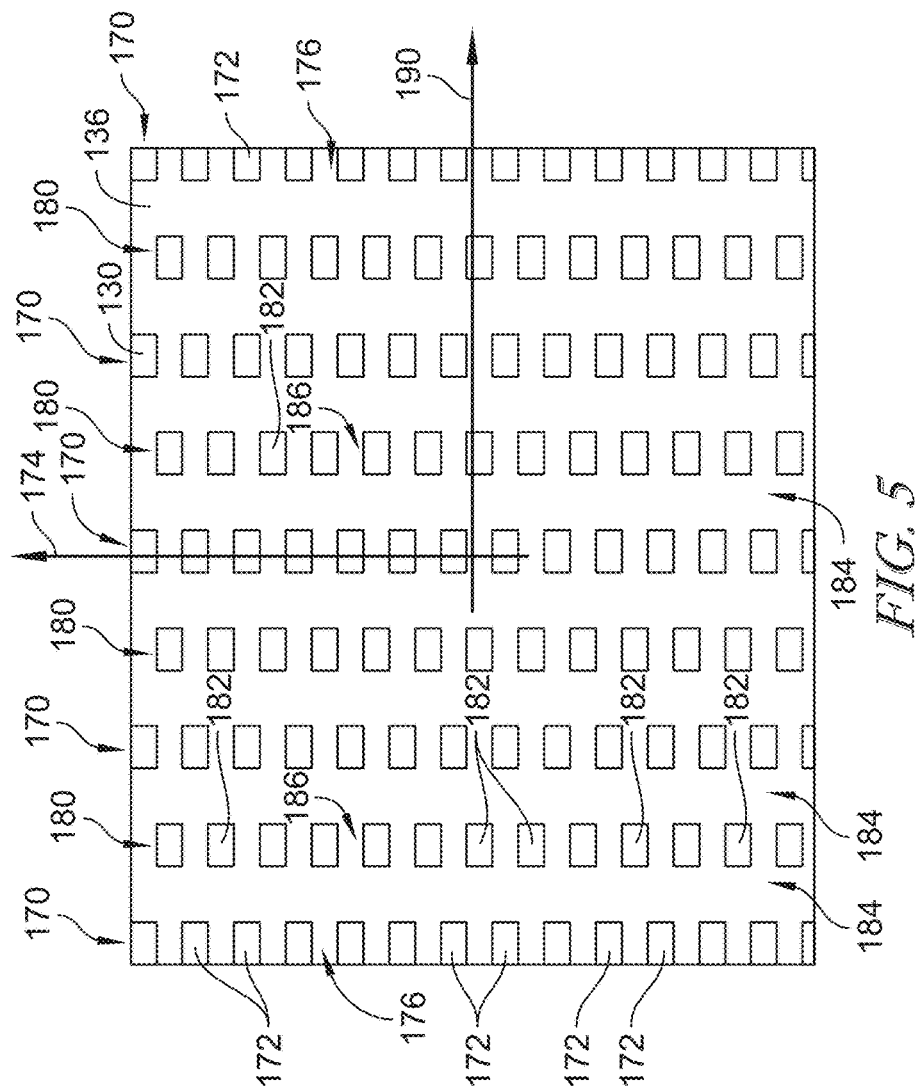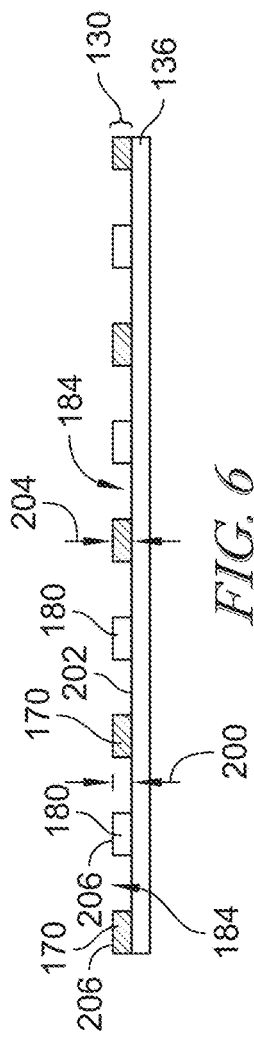

MANUFACTURING METHOD FOR INCONTINENCE DETECTION PADS HAVING WIRELESS COMMUNICATION CAPABILITY

The present application claims the benefit, under 35 U.S.C. § 119(e), of U.S. Provisional Application No. 62/850,696, filed May 21, 2019, and U.S. Provisional Application No. 62/940,965, filed Nov. 27, 2019, both of which are incorporated herein by this reference in their entirety.

BACKGROUND

The present disclosure relates to manufacturing methods for incontinence detection pads and particularly, to manufacturing methods for incontinence detection pads having wireless communication capability. More particularly, the present disclosure relates to methods of converting a manufacturing line between making standard incontinence pads and making incontinence detection pads having wireless communication capability.

Absorbent incontinence pads are placed between patients and mattresses in healthcare facilities under some circumstances when the patients are incontinent. The incontinence pads absorb the incontinence from the patients and protect the underlying mattresses and bedding from becoming soiled by the incontinence. Incontinence pads are typically less expensive than adult diapers and so, for patients that have less frequent or smaller volume incontinence events, incontinence pads may be preferred over diapers.

In recent times, efforts have been made to integrate electrical circuitry into incontinence pads and diapers to provide a signal notifying caregivers that an incontinence event has occurred. Receipt of such incontinence notification signals allows caregivers to change the pads or diapers more quickly than would otherwise be the case without such notifications. Circuitry that sends the incontinence detection signals wirelessly for receipt by an alarming system or device, such as a hospital bed and/or a nurse call system, is preferred over wired circuitry because, in such wireless systems, caregivers do not need to disconnect wires or cables from soiled incontinence detection pads and reconnect them to new, unsoiled incontinence detection pads.

In the past, healthcare facilities have used standard incontinence pads a majority of the time. In this regard, the term "standard" means incontinence pads that do not include any incontinence detection circuitry. Even at present, incontinence detection pads having incontinence detection circuitry, including circuitry with wireless communication capability, are not widely used in healthcare facilities. As a result, manufacturers of incontinence pads typically have manufacturing lines in their facilities that are dedicated to making standard incontinence pads. Such dedicated manufacturing lines are feasible from an economic standpoint because standard incontinence pads are run at very high volumes due to their prevalence in the industry. Therefore, incontinence detection pads with incontinence detection circuitry having wireless communication capability are much less in demand currently and so the manufacturing volumes are significantly lower than those of standard incontinence detection pads. As such, there is a need to be able to convert a manufacturing line back and forth between making standard incontinence pads at higher volumes and making incontinence detection pads having wireless communication capability at lower volumes.

SUMMARY

A method, system or apparatus may comprise one or more of the features recited in the appended claims and/or the following features which, alone or in any combination, may comprise patentable subject matter:

According to a first aspect of the present disclosure, a method of converting a manufacturing line between making standard incontinence pads and making incontinence detection pads that have wireless communication capability is provided. The method may include replacing a first motor that may drive at least one nip roller of a pair of nip rollers and that may be feedback controlled during manufacture of the standard incontinence pads with a second motor that may be configured to be feedback controlled more accurately than the first motor during manufacture of the incontinence detection pads. The method also may include readying an RFID tag applicator to place RFID tags on backsheet material that may be fed between the pair of nip rollers. The backsheet material may have a series of electrode traces thereon. The method may further include moving RFID tag test equipment into position on the manufacturing line to test the integrity of the electrode traces after placement of the RFID tags on the backsheet material. Still further, the method may include operating the second motor to feed the backsheet material between the pair of nip rollers and toward the RFID tag applicator, operating the RFID tag applicator to place each RFID tag across end regions of a respective electrode trace of the series of electrode traces, and operating the RFID tag test equipment to energize the RFID tag using wireless emissions and receiving return signals from each RFID tag in response to the wireless emissions. At least one of the return signals may be used by the RFID tag test equipment to determine whether the respective electrode trace forms a closed circuit rather than an open circuit. After completion of manufacturing the incontinence detection pads, the method may include replacing the second motor with the first motor, deactivating the RFID tag applicator, and moving the RFID tag test equipment away from the manufacturing line so that the manufacturing line is once again configured for manufacturing the standard incontinence pads.

In some embodiments of the first aspect, the method may further include operating a vision inspection machine that may be independent of the RFID tag test equipment to determine an actual position of a registration mark of a series of registration marks on the backsheet material as compared to a desired position of the registration mark and outputting an inspection signal from the vision inspection machine that may indicate whether the second motor should be operated to advance or retard the feed of the backsheet material between the nip rollers. Optionally, the method may further include providing the inspection signal to a programmable logic controller (PLC) and outputting a speed signal from the PLC to feedback control the second motor. If desired, the method may also include providing the speed signal from the PLC to the RFID tag applicator to feedback control the RFID tag applicator. Alternatively or additionally, the method may further include providing the speed signal from the PLC to the RFID tag test equipment to feedback control the RFID tag test equipment.

It is contemplated by this disclosure that the method of the first aspect may further include operating the RFID tag applicator to apply RFID tags to the backsheet material from a hacking web that initially may be in a Z-fold pattern and the RFID tag applicator may unfold the backing web. In such embodiments, the method may further include operating a web removal machine to remove the backing web as the RFID tags are applied to the backsheet material by the RFID applicator. Optionally, the web removal machine may include an air duct to which a negative pressure may be applied to create a vacuum that may suck the backing web into the air duct. Further optionally, during operation of the RFID tag applicator, the backing web may form a loose loop between a bin holding the backing web in the Z-fold pattern and the RFID tag applicator and the method of the first aspect may further include using a jig to manually splice a back end of one hacking web with a front end of the next hacking web.

In some embodiments of the first aspect, the method may include, after each RFID tag is applied to the backsheet by the RFID tag applicator and before each RFID tag is energized by the RFID tag test equipment, adhesively marrying the backsheet material with a top sheet material and an absorbent core material. If desired, adhesively marrying the backsheet material with the top sheet material and the absorbent core material may involve a roll-marrying operation.

After the backsheet material is adhesively married with the top sheet material and the absorbent core material, the RFID tag test equipment may be operated according to the method of the first aspect to energize each RFID tag a first time and a second time. In response to being energized the first time by the RFID tag test equipment, each RFID tag may be configured to respond by sending wirelessly a tag serial number and a status of a tamper bit of an RFID chip of the RFID tag. In response to being energized the second time by the RFID tag test equipment, each RFID tag may be configured to respond by wirelessly sending an electronic product code (EPC).

In some embodiments of the first aspect, the method may further include designating a tested RFID tag and the corresponding incontinence detection pad as a test failure if the tag serial number is not sent wirelessly from the tested RFID tag in response to the tested RFID tag being energized the first time. Alternatively or additionally, the method of the first aspect may also include designating a tested RFID tag and the corresponding incontinence detection pad as a test failure if the tag status sent wirelessly from the tested RFID tag in response to the tested RFID tag being energized the first time indicates that the respective electrode trace forms an open circuit rather than a closed circuit. Further alternatively or additionally, the method of the first aspect may include designating a tested RFID tag and the corresponding incontinence detection pad as a test failure if the EPC is not sent wirelessly from the tested RFID tag or if the EPC from the tested RFID tag does not match a predetermined tag code, in response to the tested RFID tag being energized the second time.

It is contemplated that the method of the first aspect may further include, if a tested RFID tag and the corresponding incontinence detection pad are designated as a test failure by the RFID tag test equipment, removing the rejected incontinence detection before a packaging operation and retesting the RFID tag offline by using offline RFID tag test equipment. If the tested RFID tag is determined to still be a test failure after offline retesting, the method may further include scrapping the incontinence detection pad having the twice-failing RFID tag or circuit.

In some embodiments, the method of the first aspect may further include folding the adhesively married backsheet, top sheet, and absorbent core material in a machine direction. The folding in the machine direction may occur downstream of the RFID tag test equipment, for example. The method of the first aspect also may include cutting-to-length the folded backsheet, top sheet, and absorbent core material to create cut-to-length incontinence detection pads. Optionally, the method of the first aspect may further include folding the cut-to-length incontinence detection pads in a cross direction to create ready-to-pack completed incontinence detection pads.

In some embodiments of the first aspect, moving the RFID tag test equipment into position on the manufacturing line to test the integrity of the electrode traces after placement of the RFID tags on the backsheet material may include raising/lowering the RFID tag test equipment from a lowered/raised position away from the manufacturing line to a raised/lowered, operative position.

According to a second aspect of the present disclosure, a method of manufacturing incontinence detection pads that have wireless communication capability may be provided and may include readying an RFID tag applicator to place RFID tags on backsheet material that may be fed between a pair of nip rollers. The backsheet material may have a series of electrode traces thereon. The method of the second aspect may further include operating a nip roller motor to feed the backsheet material between the pair of nip rollers and toward the RFID tag applicator, operating the RFID tag applicator to place each RFID tag across end regions of a respective electrode trace of the series of electrode traces, and operating RFID tag test equipment to energize each RFID tag using wireless emissions and receiving return signals from each RFID tag in response to the wireless emissions. At least one of the return signals may be used by the RFID tag test equipment to determine whether the respective electrode trace forms a closed circuit rather than an open circuit. The method may also include operating a vision inspection machine independent of the RFID tag test equipment to determine an actual position of a registration mark of a series of of registration marks on the backsheet material as compared to a desired position of the registration mark and outputting an inspection signal from the vision inspection machine that indicates whether the nip roller motor should be operated to advance or retard the feed of the backsheet material between the nip rollers.

In some embodiments of the second aspect, the method may further include providing the inspection signal to a programmable logic controller (PLC) and outputting a speed signal from the PLC to feedback control the nip roller motor. Alternatively or additionally, the method of the second aspect may include providing the speed signal from the PLC to the RFID tag applicator to feedback control the RFID tag applicator. Further alternatively or additionally, the method of the second aspect may include providing the speed signal from the PLC to the REM tag test equipment to feedback control the RFID tag test equipment.

It is contemplated by this disclosure that the method of the second aspect may further include operating the RFID tag applicator to apply RFID tags to the backsheet material from a hacking web that initially may be in a Z-fold pattern and the RFID tag applicator may unfold the backing web. In such embodiments, the method may further include operating a web removal machine to remove the backing web as the RFID tags are applied to the backsheet material by the RFID applicator. Optionally, the web removal machine may include an air duct to which a negative pressure may be applied to create a vacuum that may suck the backing web into the air duct. Further optionally, during operation of the RFID tag applicator, the backing web may form a loose loop between a bin holding the backing web in the Z-fold pattern and the RFID tag applicator and the method of the second aspect may further include using a jig to manually splice a back end of one backing web with a front end of the next backing web.

In some embodiments of the second aspect, the method may further include, after each RFID tag is applied to the backsheet by the RFID tag applicator and before each RFID tag is energized by the RFID tag test equipment, adhesively marrying the backsheet material with a top sheet material and an absorbent core material. If desired, adhesively marrying the backsheet material with the top sheet material and the absorbent core material may involve a roll-marrying operation.

After the backsheet material is adhesively married with the top sheet material and the absorbent core material, the RFID tag test equipment may be operated according to the method of the second aspect to energize each RFID tag a first time and a second time. In response to being energized the first time by the RFID tag test equipment, each RFID tag may be configured to respond by sending wirelessly a tag serial number and a status of a tamper bit of an RFID chip of the RFID tag. In response to being energized a second time by the RFID tag test equipment, each RFID tag may be configured to respond by wirelessly sending an electronic product code (EPC).

In some embodiments of the second aspect, the method may further include designating a tested RFID tag and the corresponding incontinence detection pad as a test failure if the tag serial number is not sent wirelessly from the tested RFID tag in response to the tested RFID tag being energized the first time. Alternatively or additionally, the method of the second aspect may further include designating a tested RFID tag and the corresponding incontinence detection pad as a test failure if the tang status sent wirelessly from the tested RFID tag in response to the tested RFID tag being energized the first time indicates that the respective electrode trace forms an open circuit rather than a closed circuit. Further alternatively or additionally, the method of the second aspect may further include designating a tested RFID tag and the corresponding incontinence detection pad as a test failure if the EPC is not sent wirelessly from the tested RFID tag or if the EPC from the tested RFID tag does not match a predetermined tag code, in response to the tested RFID tag being energized the second time.

It is contemplated that the method of the second aspect may further include, if a tested RFID tag and the corresponding incontinence detection pad are designated as a test failure by the RFID tag test equipment, removing the rejected incontinence detection from a packaging operation and manually retesting the RFID tag by using an offline RFID tag test equipment. If the tested RFID tag is determined to still be a test failure after manual retesting, the method may further include scrapping the incontinence detection pad having the twice-failing RFID tag.

In some embodiments, the method of the second aspect may further include folding the adhesively married backsheet, top sheet, and absorbent core material in a machine direction. The folding in the machine direction may occur downstream of the RFID tag test equipment, for example. The method of the second aspect may also include cutting-to-length the folded backsheet, top sheet, and absorbent core material to create cut-to-length incontinence detection pads. Optionally, the method of the second aspect may further include folding the cut-to-length incontinence detection pads in a cross direction to create ready-to-pack completed incontinence detection pads.

In some embodiments of the first aspect and the second aspect, cutting-to-length the folded backsheet, top sheet and absorbent core may sever a sacrificial trace portion of the electrode trace from each of the cut-to-length incontinence detection pads with the sacrificial trace portion remaining on a next adjacent incontinence detection pad and leaving two separate electrode trace portions for incontinence detection on the cut-to-length incontinence detection pads.

According to a third aspect of the present disclosure, a method of manufacturing incontinence detection pads that have wireless communication capability may be provided and may include readying an RFID tag applicator to place RFID tags on backsheet material that may be fed between a pair of nip rollers. The backsheet material may have a series of electrode traces thereon. The method of the third aspect may also include operating a nip roller motor to feed the backsheet material between the pair of nip rollers and toward the RFID tag applicator, operating the RFID tag applicator to place each RFID tag across regions of a respective electrode trace of the series of electrode traces, and operating RFID tag test equipment to energize each RFID tag a first time and a second time using wireless emissions and receiving return signals from each RFID tag in response to the wireless emissions. In response to being energized the first time by the RFID tag test equipment, each RFID tag may be configured to respond by sending first data wirelessly and, in response to being energized a second time by the RFID tag test equipment, each RFID tag may be configured to respond by sending second data wirelessly. The second data may be different than the first data.

In some embodiments of the method of the third aspect, the first data may include at least a tag serial number and a status of a tamper bit of an RFID chip of the RFID tag and the second data may include at least an electronic product code (EPC). The method of the third aspect may further include designating a tested RFID tag and the corresponding incontinence detection pad as a test failure if the tag serial number is not sent wirelessly from the tested. RFID tag in response to the tested RFID tag being energized the first time. Alternatively or additionally, the method of the third aspect may include designating a tested RFID tag and the corresponding incontinence detection pad as a test failure if the tag status sent wirelessly from the tested RAD tag in response to the tested RFID tag being energized the first time indicates that the respective electrode trace forms an open circuit rather than a closed circuit. Further alternatively or additionally, the method of the third aspect may include designating a tested RFID tag and the corresponding incontinence detection pad as a test failure if the EPC is not sent wirelessly from the tested RFID tag or if the EPC from the tested RFID tag does not match a predetermined tag code, in response to the tested RFID tag being energized the second time.

In connection with the third aspect, if a tested RFID tag and the corresponding incontinence detection pad are designated as a test failure by the RFID tag test equipment, the method may further include removing the rejected incontinence detection from a packaging operation and manually retesting the RFID tag by using offline RFID tag test equipment. If the tested RFID tag is determined to still be a test failure after manual retesting, the method of the third aspect may further include scrapping the incontinence detection pad having the twice-failing RFID tag.

In some embodiments, the method of the third aspect may further include operating a registration mark detector independent of the RFID tag test equipment to determine an actual position of a registration mark of a series of registration marks on the backsheet material as compared to a desired position of the registration mark and outputting a signal from the registration mark detector that indicates whether a nip roller motor controller should be operated to advance or retard the teed of the backsheet material between the nip rollers. Optionally, the method of the third aspect may further include providing the signal to a programmable logic controller (PLC) and outputting a speed signal from the PLC to feedback control the nip roller motor. If desired, the method of the third aspect may also include providing the speed signal from the PLC to the RFID tag applicator to feedback control the RFID tag applicator. Alternatively or additionally, the method of the third aspect may include providing the speed signal from the PLC to the MD tag test equipment to feedback control the RFID tag test equipment.

It is contemplated by this disclosure that the method of the third aspect may further include operating the RFID tag applicator to apply RFID tags to the backsheet material from a backing web that initially may be in a packaged state and the RFID tag applicator may unpackage the backing web. In such embodiments of the third aspect, the method may further include operating a web removal machine to remove the backing web as the RFID tags are applied to the backsheet material by the RFID applicator. Optionally, the web removal machine may include an air duct to which a negative pressure may be applied to create a vacuum that may suck the backing web into the air duct or the backing web may be re-rolled by the web removal machine. Further optionally, during operation of the RFID tag applicator, the method of the third aspect may further include using a jig to manually splice a hack end of one backing web with a front end of the next backing web.

In some embodiments of the third aspect, the method may further include adhesively marrying the backsheet material with a top sheet material and an absorbent core material prior to operating the RFID test equipment. If desired, adhesively marrying the backsheet material with the top sheet material and the absorbent core material may involve a roll-marrying operation.

It is contemplated by this disclosure that the method of the third aspect may further include folding the adhesively married backsheet, top sheet, and absorbent core material in a machine direction. The folding in the machine direction may occur downstream of the RFID tag test equipment, for example. The method of the third aspect may also include cutting-to-length the folded backsheet, top sheet, and absorbent core material to create cut-to-length incontinence detection pads. Optionally, the method of the third aspect may include folding the cut-to-length incontinence detection pads in a cross direction to create ready-to-pack completed incontinence detection pads.

According to a fourth aspect of the present disclosure, a method of manufacturing incontinence detection pads that have wireless communication capability may include printing an electrode trace on a backsheet material. The method may also include placing a radio-frequency identification (RFID) tag on the backsheet material so that the RFID tag is electrically coupled to the electrode trace. The method may also include adhering a moisture absorbent core to a top sheet material with a layer of adhesive arranged in a spaced checkerboard configuration. The method may also include adhering the top sheet material and moisture absorbent core to the backsheet material to secure the moisture absorbent core between the top sheet material backsheet material.

In some embodiments of the fourth aspect, the method may also include forming the spaced checkboard configuration with a first row of adhesive marks spaced apart from a second row of adhesive marks. The method may also include forming the first row of adhesive marks with a first plurality of spaced apart marks. The method may also include forming the second row of adhesive marks with a second plurality of spaced apart marks. The method may also include offsetting the first plurality of spaced apart marks from the second plurality of spaced apart marks. The method may also include spacing the first row of adhesive marks from the second row of adhesive marks in a first direction. The method may also include spacing the first plurality of spaced apart marks in a second direction that is perpendicular to the first direction. The method may also include spacing the second plurality of spaced apart marks in the second direction.

It may be contemplated by the method of the fourth aspect that the backsheet material is formed with a laminate of polyethylene on a non-woven layer. The method may also include roll-marrying the top sheet material and moisture absorbent core to the backsheet material. The method may also include folding the adhesively married backsheet material, top sheet material, and moisture absorbent core in a machine direction. The method may also include cutting-to-length the folded backsheet material, top sheet material, and moisture absorbent core to create cut-to-length incontinence detection pads. The method may also include folding the cut-to-length incontinence detection pads in a cross direction to create ready-to-pack completed incontinence pads. The method may also include energizing the RFID tang after the top sheet material and moisture absorbent core are adhered to the backsheet material.

It may be desired that the method of the fourth aspect includes adhering the top sheet material and the moisture absorbent core to the backsheet material along an edge of the backsheet material. The method may also include adhering the top sheet material and the moisture absorbent core to the backsheet material along all four edges of the backsheet material.

Optionally, the method of the fourth aspect may include printing a plurality of electrode traces on the backsheet material. The method may also include electrically coupling the RFID tag to the plurality of electrode traces.

According to a fifth aspect of the present disclosure, an incontinence detection pad having wireless communication capability may include a backsheet material including an electrode trace. A radio-frequency identification (RFID) tag may be placed on the backsheet material so that the RFID tag is electrically coupled to the electrode trace. A moisture absorbent core may be adhered to a top sheet material with a layer of adhesive arranged in a spaced checkerboard configuration. The top sheet material and moisture absorbent core may be are adhered to the backsheet material to secure the moisture absorbent core between the top sheet material backsheet material.

In some embodiments of the fifth aspect, the spaced checkboard configuration may include a first row of adhesive marks spaced apart from a second row of adhesive marks. The first row of adhesive marks may include a first plurality of spaced apart marks. The second row of adhesive marks may include a second plurality of spaced apart marks. The first plurality of spaced apart marks may be offset from the second plurality of spaced apart marks. The first row of adhesive marks may be spaced from the second row of adhesive marks in a first direction. The first plurality of spaced apart marks may be spaced in a second direction that is perpendicular to the first direction. The second plurality of spaced apart marks may be spaced in the second direction.

It may be contemplated by the fifth aspect that the backsheet material may include a laminate of polyethylene on a non-woven layer. The top sheet material and moisture absorbent core may be roll-married to the backsheet material. The top sheet material and the moisture absorbent core may be adhered to the backsheet material along an edge of the backsheet material. The top sheet material and the moisture absorbent core may be adhered to the backsheet material along all four edges of the backsheet material. The pad may include a plurality of electrode traces printed on the backsheet material. The RFID tag may be electrically coupled to the plurality of electrode traces.

According to a sixth aspect of the present disclosure, a method of manufacturing incontinence detection pads may include adhering a moisture absorbent core to a top sheet material with a layer of adhesive arranged in a spaced checkerboard configuration. The method may also include adhering the top sheet material and moisture absorbent core to a backsheet material to secure the moisture absorbent core between the top sheet material backsheet material.

In some embodiments of the sixth aspect, the method may also include forming the spaced checkboard configuration with a first row of adhesive marks spaced apart from a second row of adhesive marks. The method may also include forming the first row of adhesive marks with a first plurality of spaced apart marks. The method may also include forming the second row of adhesive marks with a second plurality of spaced apart marks. The method may also include offsetting the first plurality of spaced apart marks from the second plurality of spaced apart marks. The method may also include spacing the first row of adhesive marks from the second row of adhesive marks in a first direction. The method may also include spacing the first plurality of spaced apart marks in a second direction that is perpendicular to the first direction. The method may also include spacing the second plurality of spaced apart marks in the second direction.

According to a seventh aspect of the present disclosure, an incontinence detection pad may include a backsheet material. A moisture absorbent core may be adhered to a top sheet material with a layer of adhesive arranged in a spaced checkerboard configuration. The top sheet material and moisture absorbent core may be adhered to the backsheet material to secure the moisture absorbent core between the top sheet material backsheet material.

In some embodiments of the seventh aspect, the spaced checkboard configuration may include a first row of adhesive marks spaced apart from a second row of adhesive marks. The first row of adhesive marks may include a first plurality of spaced apart marks. The second row of adhesive marks may include a second plurality of spaced apart marks. The first plurality of spaced apart marks may be offset from the second plurality of spaced apart marks. The first row of adhesive marks may be spaced from the second row of adhesive marks in a first direction. The first plurality of spaced apart marks may be spaced in a second direction that is perpendicular to the first direction. The second plurality of spaced apart marks may be spaced in the second direction.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which:

FIG. 5 is a top plan view of the adhesive layer shown in FIG. 4 having adhesive marks in a spaced checkerboard configuration; and FIG. 6 is a side elevation view of the adhesive layer shown in FIG. 5 and having channels formed between the adhesive marks.

DETAILED DESCRIPTION

Figure 1A:
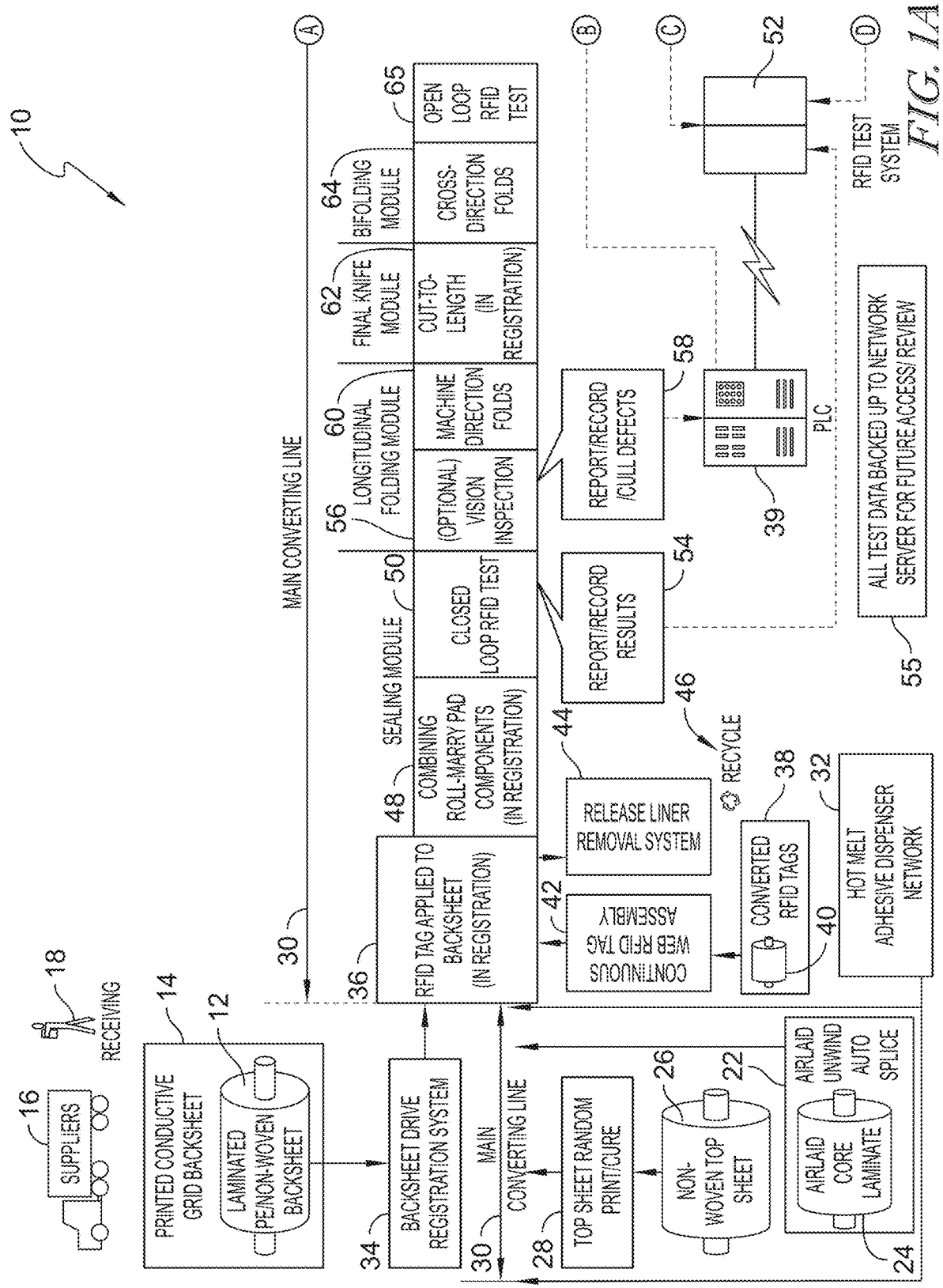
FIGS. 1A and 1B together form a block diagram of a manufacturing method for making incontinence detection pads having wireless communication capability and for testing electrical circuitry of the incontinence detection pads during manufacture.
Figure 1B:
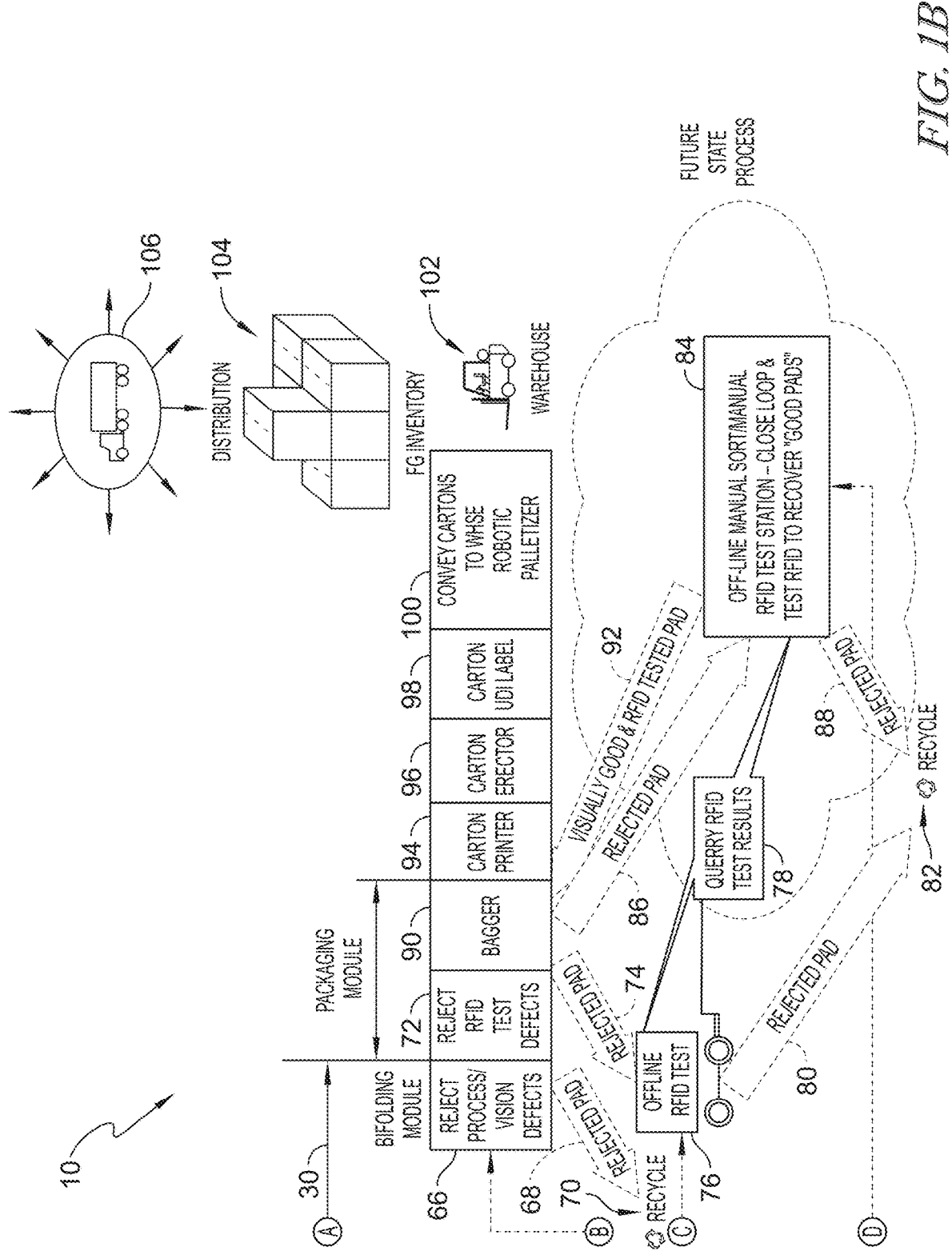

As shown diagrammatically in FIGS. 1A and 1B, a method 10 for manufacturing incontinence detection pads having wireless communication capability includes printing a series of electrode traces on backsheet material 12 as indicated at block 14 of FIG. 1A. The term electrode trace is referred to as conductive grid in block 14 and these terms are used herein interchageably. Examples of suitable electrode traces or conductive grids within the scope of this disclosure can be found in U.S. Patent Application Publication No. 2018/0021184 A1 (see particularly FIGS. 36, 39, 45 and 61-62D and the related description); 2017/0246063 A1 (see particularly FIGS. 9 and 12A-13D and the related description); and 2019/0060137 (see particularly FIGS. 9A, 10, 11, 14A-18, 25 and 31A-31N and the related description), each of which is hereby incorporated by reference herein in its entirety to the extent not inconsistent with the present disclosure which shall control as to any inconsistencies.

In the illustrative example, a roll of backsheet material 12 is provided by one or more suppliers 16 without having any electrode traces printed thereon. One representative supplier 16 is Avintiv Technical Nonwovens (formerly Fiberweb) of Old Hickory, Tennessee. The printer associated with block 14 receives the rolls of backsheet material 12 as indicated at receiving icon 18 in FIG. 1A. The printer unrolls the received backsheet material 12, prints the series of electrode traces thereon, and then re-rolls the backsheet material 12 for further handling. At block 14, an optional registered splice operation may also be performed, as needed, so that the end of one roll of backsheet material 12 is attached to the beginning of the next roll of backsheet material 12 in registration or in close proximity. In some embodiments, the backsheet material includes a laminate of a polyethylene sheet or layer and a spunbond, nonwoven layer. A representative printer associated with block 14 is Tapecon of Buffalo, New York which employs print cylinders or plates and conductive ink from Sun Chemical Corporation of Parsippany, New Jersey to print the electrode traces on the received backsheet material 12.

In connection with method 10, it was discovered that corona treatment was not required to suitably adhere the ink to the polyethylene layer.

At block 14 of method 10, the backsheet material 12 undergoes a random print and cure process. In particular, at block 14 various icons and trademark information, such as a corporate logo and the product name of the incontinence detection pads, is printed on the spunbond, nonwoven layer of the backsheet material 12. In some embodiments, the printing operation at block 14 may employ a bottom printing technique in which an impression roller beneath the backsheet material 12 applies a UV curing ink to the backsheet material 12. A solvent or water-based ink may be used in other embodiments. In one embodiment contemplated by this disclosure, the trademarks HILL-ROM® and WATCH-CARE®, along with a water droplet icon (e.g., see FIGS. 18A-19D of U.S. Patent Application Publication No. 2017/0246063 which is already incorporated by reference herein) are printed on the backsheet material 12 at block 20. In another embodiment, the backsheet PE material 12 is supplied pre-printed with various icons and trademark information.

Block 20 indicates that the printing is "random" because the trademarks and water droplet icons are each printed repeatedly on backsheet 12 in rows along the machine direction (i.e., direction of movement of the backsheet material 12 as it unrolls and moves through the manufacturing equipment of method 10) and then, when the backsheet material 12 and other layers to be discussed below are cut to form individual incontinence detection pads, the locations of the individual trademarks on the backsheet will vary from pad to pad. After the impression roller applies the ink to backsheet material 12, UV light is used to cure the ink on the backsheet material 12. One representative manufacturer to perform the random print and UV cure process of block 20 is Presto Absorbent Products of Eau Claire, Wisconsin.

As indicated at block 22 a roll of airlaid core laminate material 24 is unwound and is also auto spliced, as needed, so that the end of one roll of airlaid core laminate material 24 is attached to the beginning of the next roll of airlaid core laminate material 24. One representative supplier of equipment necessary to laminate the airlaid core laminate material is Web Industries of Fort Wayne, Indiana Simultaneously with unrolling of material 24, a roll of nonwoven top sheet material 26 is unrolled and undergoes a random print and cure process as indicated at block 28. In some embodiments, the printing operation at block 28 employs a top printing technique in which an impression roller above the top sheet material 26 applies a UV curing ink to the top sheet material 26. A solvent or water-based ink may be used in other embodiments. After the impression roller applies the ink to top sheet material 26, the ink undergoes a curing process on the top sheet material 26.

In some embodiments, at block 28 head and feet indicia or icons are printed on the nonwoven top sheet material 26. See FIGS. 10A-12C, 13A-13C and 14A-17D of U.S. Patent Application Publication No. 2017/0246063, which is already incorporated by reference herein, for examples of head and feet icons that are contemplated as being printed on the top sheet material 26 at block 28. Similar to block 20, block 28 indicates that the printing is "random" because the head and feet icons are each printed repeatedly on top sheet 26 in rows along the machine direction and then, when the back sheet material 12, top sheet material 26, and airlaid core laminate material 24 is cut to form individual incontinence detection pads, the locations of the individual head and feet icons on the top sheet will vary from pad to pad. The head icons and feet icons are located near the top edges and bottom edges, respectively, of the incontinence detection pads to provide caregivers an indication as to how the incontinence detection pads should be oriented when placed beneath a patient in use.

After the print and cure operation at block 28, the unrolled airlaid core laminate material 24 and the top sheet material 26 enter a main converting line 30 that includes a hot melt adhesive dispenser network as indicated at block 32 of FIG. 1A. The hot melt adhesive dispenser network 32 includes one or more supplies, containers, or reservoirs of adhesive material that is distributed along the main converting line 30 at various locations for slot coating and/or spray coating the components of the incontinence detection pads together. Thus, a series of hoses lead from the adhesive reservoirs to the main converting line 30 are used for dispensing the adhesive. In some embodiments, an SSMMS barrier layer is laminated to the airlaid core material inline at the beginning of main converting line 30 which negates the need to laminate the barrier layer to the airlaid core material at block 22. After the top sheet material 26 and the airlaid core material 24 reach the main converting line 30, adhesive is slot coated onto the top sheet material 26 for adhering the airlaid core laminate material 24 thereto. See, for example, the discussion in U.S. Patent Application Publication No. 2018/0021184, already incorporated by reference herein, regarding slot coating and spray coating of adhesive onto various portions of incontinence detection pads (particularly at paragraphs [0326]-[328] and [0334]). See also U.S. Patent Application Publication No. 2019/0060137, also already incorporated by reference herein, regarding slot coating and spray coating of adhesive onto various portion of incontinence detection pads (particularly at paragraphs [0165], [0169], [0171], [0172], [0176], [0209], [0211], [0292] and [0297]). In some embodiments, the hot melt adhesive dispenser network 32 is a Nordson® adhesive dispensing system available from Nordson Corporation of West Lake, Ohio.

In some embodiments, the main converting line 30 (aka the underpad line or underpad converting line) is of the type made by Curt G. Joa, Inc. of Sheboygan Falls, Wisconsin; GDM SpA of Offanengo, Italy; or Fameccanica.Data SpA, Pescara, Italy. The main converting line 30 includes a backsheet drive registration system 34 that includes a pair of nip rollers through which the backsheet material 12 is fed after the random print/UC cure 20 operation. One of the nip rollers is driven by a motor that is feedback controlled by a signal from a programmable logic controller (PLC) 39. In some embodiments, PLC 39 may be an Allen-Bradley® ControlLogix PLC controller available from Rockwell Automation, Inc. of Milwaukee, Wisconsin.

When standard incontinence pads are being manufactured on converting line 30, the motor used to drive the nip rollers is an Allen-Bradley® motor in some embodiments. However, it was determined that a higher accuracy motor is needed when incontinence detection pads having wireless communication capability are being manufacture on converting line 30. In this regard, a suitable motor for driving the nip rollers is made by Bosch. Thus, the present disclosure contemplates that to convert a manufacturing line between making standard incontinence pads and making incontinence detection pads that have wireless communication capability, a first motor (e.g., an Allen Bradley® motor) that drives at least one nip roller of a pair of nip rollers and that is feedback controlled during manufacture of the standard incontinence pads with a second motor (e.g., a Bosch® motor) that is configured to be feedback controlled more accurately than the first motor during manufacture of the incontinence detection pads.

After the backsheet material 12 is fed through the nip rollers of backsheet drive registration system 34, RFID tags are applied to the backsheet material 12 as indicated at block

36 of FIG. 1A. An RFID tag applicator is operated at block 36 to place the RFID tags at end regions of the electrode traces on the backsheet material 12. For additional details of such an RFID tag applicator see U.S. Pat. No. 8,453,700 which is hereby incorporated by reference herein in its entirety to the extent not inconsistent with the present disclosure which shall control as to any inconsistencies. For examples of the locations at which RFID tags are placed relative to the electrode traces of backsheet material 12, see U.S. Patent Application Publication No. 2018/0021184 A10 (see particularly FIGS. 31, 34A, 34B, 36, 39, 61A-62D, and 69G and the related description), 2017/0246063 A1 (see particularly FIGS. 9 and 12A-13D and the related description) and 2019/0060137 (see particularly FIGS. 9A, 9C, 10, 14A-14C, 14F, 15-18, 21 and 31A-31N and the related description), each of which is already incorporated by reference herein.

In some embodiments, the RFID tags are supplied on a release liner having an accordion or Z-fold pattern as indicated diagrammatically at block 38. Suitable RFID chips for use in the RFID tags include, for example, model nos. G2iL+ chips. In some embodiments, Identiv, Inc. of Fremont, California die cuts thin aluminum layers to form the antennae of the RFID tags and then places the antennae, the RFID chips, and resistors (see FIGS. 5B-7D of U.S. Publication No. 2019/0060137, and the related discussion) on a release liner. The release liner with the antennae, RFID chips, and resistors is then provided to Innovize, Inc. of St. Paul, Minnesota which applies foam and conductive adhesive to the release liner at the appropriate locations (see FIG. 57 of U.S. Patent Application Publication No. 2018/0021184 A1, and the related discussion and see FIGS. 4A-4D of U.S. Patent Application Publication No. 2019/0060137, and the related discussion). In other embodiments, in-line application of foam to the RFID tags is accomplished on the conversion line 30 using a line-side diaper tape tab converter. The RFID tags on the Z-fold release liner are shown diagrammatically and are referred to as converted RFID tags 40 in block 38.

The converted RFID tags 40 including RFID tags and the associated Z-fold release liner are provided in a Gaylord bin and then an unwind operation is performed as indicated diagrammatically at block 42 to provide a continuous web RFID tag assembly to the tag applicator of block 36. The unwind operation involves a rotating mandrel around which the release liner of the converted RFID tans 40 is wrapped in a helical pattern so as to straighten out the Z-fold release liner prior to introduction into the tag applicator. Between the Gaylord bin of block 38 and the rotating mandrel of block 42 leading to the RFID tag applicator of block 36, the release liner forms a large loose loop that hangs downwardly. By providing the loose loop in this manner, there is enough time to splice the trailing end of one Z-fold release liner with the leading end of the next Z-fold release liner without the need to stop the rotating mandrel. During the splice operation, therefore, the rotating mandrel pulls in the loose loop of release liner material but the intention is that the splice operation is completed before the loose loop gets pulled taut by the rotating mandrel.

In some embodiments, the tag applicator includes vision inspection equipment such as a camera that is used to monitor for proper placement of the RFID tags on the backsheet material 12. If the vision inspection equipment detects that at least two RFID tags in a row are missing, then the tag applicator sends a signal to shut down the main converting line 30 and production of incontinence detection pads comes to a halt. This allows for the stock of converted RFID tags 40 to be checked for problems and replaced with new stock, if needed. The proper positioning of the release liner material on the no-longer-rotating mandrel can also be checked and adjusted, as needed.

Figure 2:
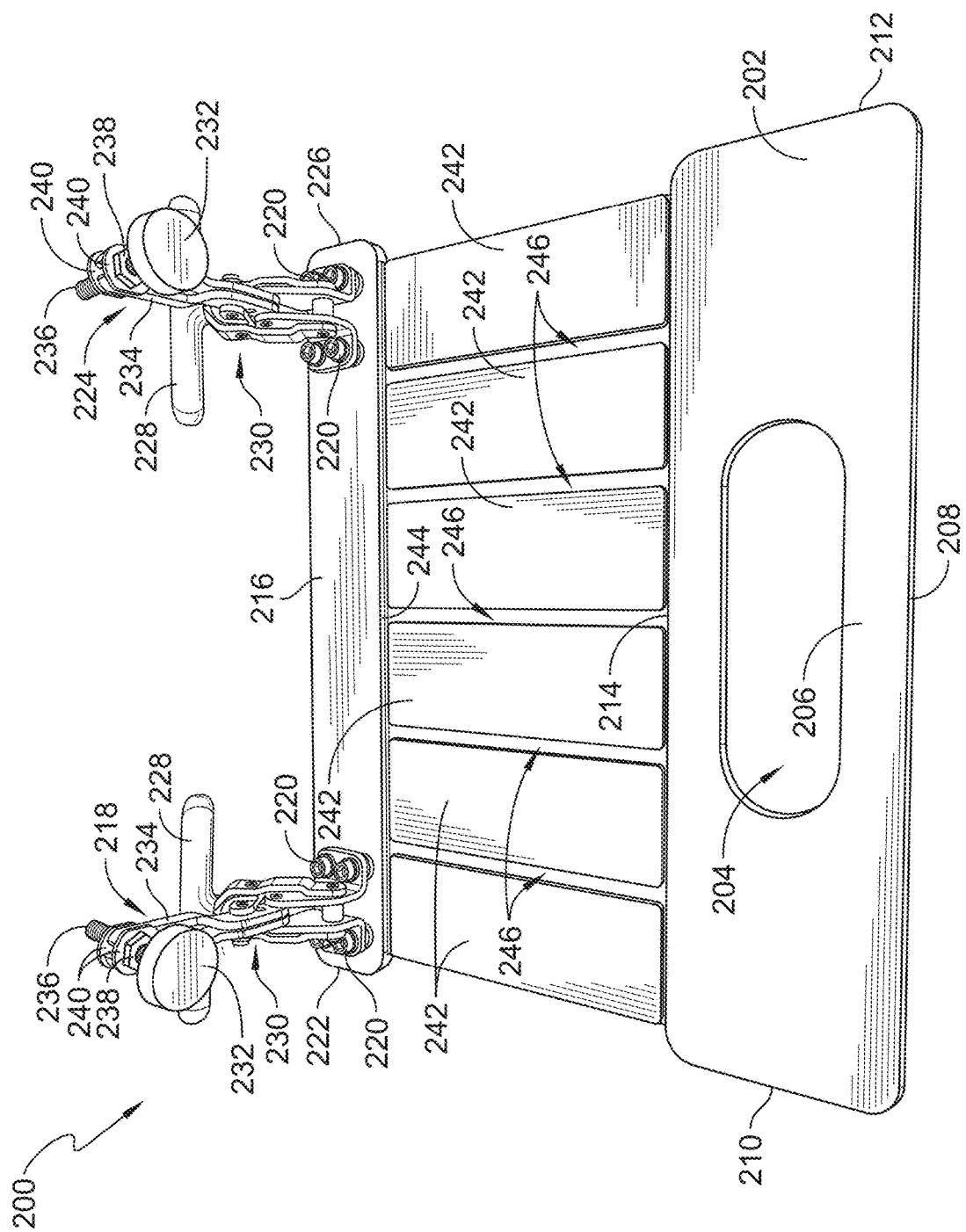
FIG. 2 is a perspective view of a jig that is used during the manufacturing process to splice webs containing radio frequency identification (RFID) tags together when a first web of RFID tags is nearing its end.
Figure 3:
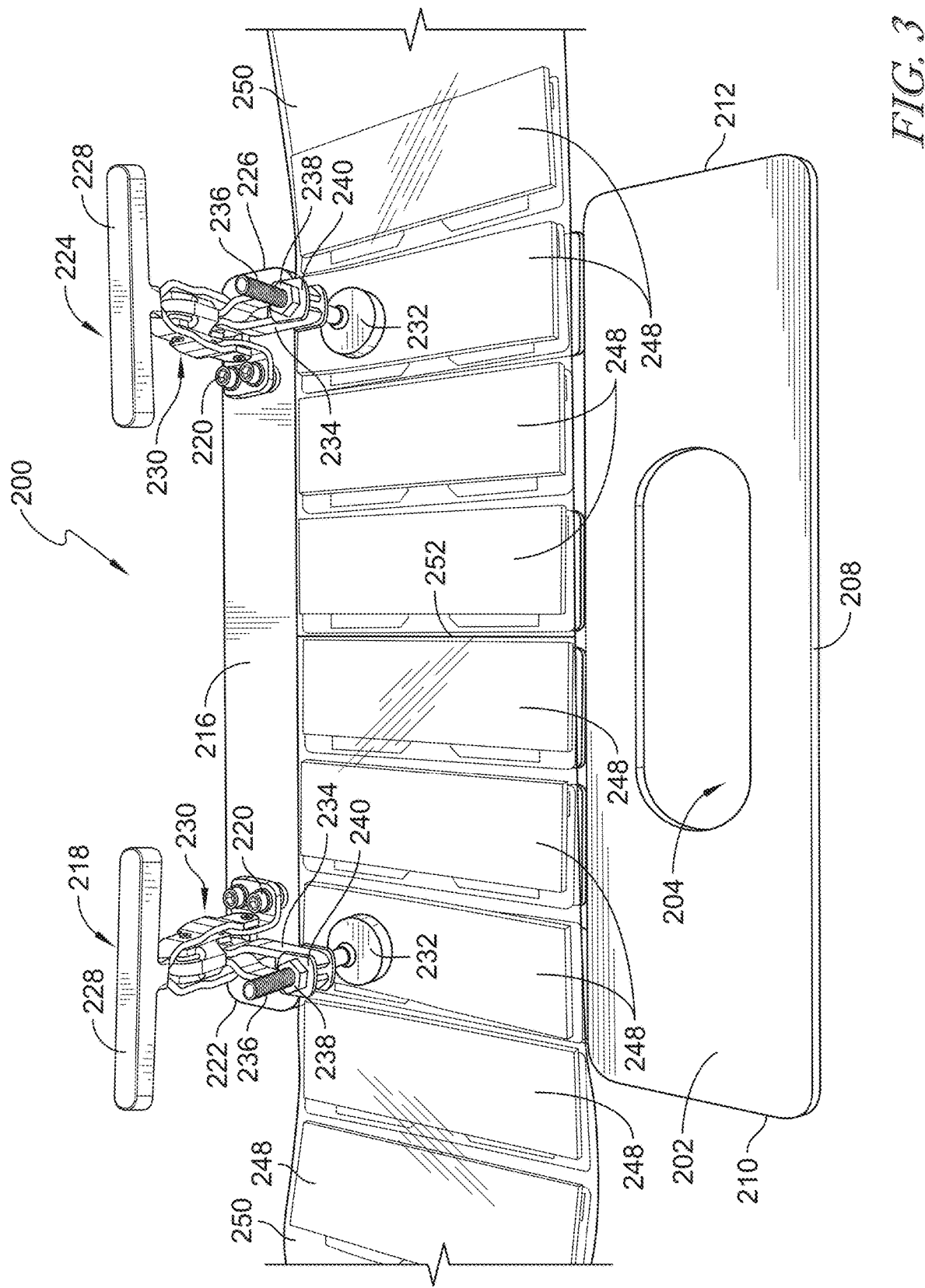
FIG. 3 is a perspective view of the jig of FIG. 2 showing the jig clamping first and second webs of RFID tags in place for splicing together.

Referring now to FIGS. 2 and 3, a jig 200 that is used during the splice operation of the trailing end of one Z-fold release liner with the leading end of another Z-fold release release liner includes a generally rectangular front plate 202 having an elongated hand hole 204 formed therethrough to provide plate 202 with a grip portion 206 defined between hand hole 204 and a front edge 208 of plate 202. Hand hole 204 is sufficiently large for an operator to place four fingers therethrough. In the illustrative embodiment of jig 200, hand hole 204 is located about midway between first and second side edges 210, 212 of plate 202 and about midway between front edge 208 and a rear edge 214 of plate 202. In other embodiments, hand hole 204 is located elsewhere on plate 202 or is omitted altogether. Each of edges 208, 210, 212, 214 is substantially straight (e.g., within manufacturing tolerances) with plate 202 having rounded corner regions interconnecting the adjacent edges 208, 210, 212 214.

Jig 200 also includes a generally rectangular rear plate 216, a first clamp 218 secured to plate 216 with fasteners such as illustrative screws 220 adjacent a first end edge 222 of plate 216, and a second clamp 224 also secured to plate 216 with fasteners such as screws 220 adjacent a second end edge 226 of plate 216. Clamps 218, 224 each include an actuating handle 228, an overcenter linkage 230, and a clamping pad 232. Clamping pads 232 are mounted to distal ends of respective forked links 234 of overcenter linkage 230 with a threaded bolt 236 and a pair of nuts 238. Oblong washers 240 are interposed between each nut 238 and the respective forked link 234. Bolts 236 are substantially perpendicular (e.g., within plus or minus 10% of 90 degrees) to the long dimension of respective forked links 234. Rotation of bolts 236 adjusts the position of clamping pads 232 relative to the respective forked links 234. Nuts 238 are tightened against washers 240 and the ends of forked links 234 once clamping pads 232 are at the desired positions relative to forked links 234.

As shown in FIG. 2, jig 200 includes six tag alignment plates 242 situated between plates 202, 216 and interconnecting plates 202, 216. Thus, opposite ends of each plate 242 are coupled to rear edge 214 of plate 202 and a front edge 244 of plate 216. Plates 242 are spaced apart resulting in gaps 246 being defined between each pair of adjacent plates 242. Plates 242 are spaced apart by substantially the same distance that RFID tags 248 on release liner 250 are spaced as shown in FIG. 3. Thus, for example, three RFID tans 248 at the trailing end of one release liner 250 are placed in jig 200 so as to overlie the three respective plates 242 at one side of jig 200 and three RFID tags 248 at the leading end of the next release liner 250 are placed in jig 200 so as to overlie the three respective plates 242 at the other side of jig 200 as shown in FIG. 3.

After the release liners 250 are placed in jig 200 in end-to-end relation, handles 228 of clamps 218, 224 are moved from a first position, shown in FIG. 2, to a second position, shown in FIG. 3, to actuate linkages 230 to move pads 232 into clamping contact with the RFID tags 248 at the opposite ends of jig 200, thereby securing the RFID tags 248 and release liners 250 in place in jig 200. Such an arrangement of RFID tag placement in jig 200 results in a split line 252 being formed between the trailing end of one release liner 250 and the leading end of the next release liner 250. Tape is then used at the split line 252 to interconnect the adjacent release liners 250 together so that the interconnected release liners 250 with tags 248 thereon can be pulled seamlessly onto the rotating mandrel of block 42 and wound onto the mandrel in the helical pattern described above.

Referring once again to FIG. 1A, as the RFID tags 248 are separated from the accompanying release liner 250 and attached to the backsheet material 12, the release liner 250 is pulled away from the main converting line 30 by a release liner removal system 44 for eventual recycling as indicated by icon 46. In some embodiments, the release liner removal system 44 comprises a web removal machine such as an air duct to which a negative pressure is applied to create a vacuum that sucks the release liner 250, which is sometimes referred to as a backing web herein, into the air duct. The release liner 250 vacuumed into the air duct of removal system 44 is collected in a recycling receptacle, in some embodiments, for eventual transport to a recycling facility.

After the RFID tags 248 are coupled to the backsheet material 12 at block 36, the backsheet material 12 having RFID tags 248 is combined with the top sheet 26 and the airlaid core laminate material 24 in a roll-marrying operation as indicated at block 48. The roll-marrying operation includes placing generally rectangular sections of spaced-apart airlaid core laminate material 24 on the backsheet material 12 at proper locations based on a series of registration marks provided on the backsheet material 12. For example, see registration mark 254 in FIG. 9 and the related discussion at paragraph [0131] of U.S. Patent Application Publication No. 2017/0246063 A1; see registration mark 3144 in FIG. 31 and the related discussion at paragraph [0323] of U.S. Patent Application Publication No. 2018/0021184 A1; and see registration marks 141b, 141b' in FIGS. 9A and 25, respectively, and the related discussion at paragraphs [0202] and [0299], respectively, of U.S. Patent Application Publication No. 2019/0060137. The same registration marks on backsheet material 12 are also used in connection with the proper placement of RFID tags 248 in some embodiments.

In the completed incontinence detection pads, the rectangular sections of airlaid core laminate material 24 is not as long and is not as wide as the top sheet material 26 and backsheet material 12 between which the airlaid core laminate material 24 is sandwiched. Thus, there are gaps between the rectangular sections of airlaid core laminate material 24 after they are deposited on the backsheet material 12 during the roll-marrying operation of block 48. Furthermore, the hot melt adhesive dispenser network 32 spray coats and slot coats the adhesive at the appropriate locations of backsheet material 12, airlaid core laminate material 24, and top sheet material 26 during the roll-marrying operation of block 48.

After the material 12, 24, 26 is roll-married together at block 48 to form a continuous web, the RFID tags of the resulting continuous web then undergo a closed loop RFID test as indicated at block 50 of FIG. 1A. In some embodiments, the equipment to perform the RFID test at block 50 includes a Voyantic TAGSURANCE™ measurement system available from Voyantic Ltd. of Espoo, Finland. According to the present disclosure, the RFID test equipment of block 50 is raised upwardly above the converting line 30 during manufacture of standard incontinence pads and is lowered downwardly into communicative proximity with the RFID tags of the continuous web moving along the converting line 30 during manufacture of incontinence detection pads having wireless communication capability. For example, the RFID test equipment of block 50 is suspended from a ceiling or an overhead framework of the manufacturing facility in which converting line 30 is located.

Converting line 30 operates at high speed which, for purposes of this disclosure, is considered to be 150 to 900 feet per minute (FPM) pad processing rates of the continuous web which correlates to producing 50 to 300 pads per minute with the incontinence detection pads produced by method 10 being substantially rectangular in shape with width and length dimensions of about 30 inches by about 36 inches. It is desired that the RFID test equipment at block 50 be operational anytime speeds within this range are reached which equates to a test process window time of 200 milliseconds to 1.2 seconds per pad.

In use during manufacture of incontinence detection pads, the RFID test equipment of block 50 emits wireless energy in two separate bursts to activate the RFID chip of the RFID tag passing thereunder and reads the backscattered reflected signals emitted from the RFID tag in response. In this regard, the RFID test equipment of block 50 recognizes features (e.g., electrode trace pattern and/or registration mark) contained on the continuous web that indicates an RFID tag is forthcoming on the web and triggers the test system to function as required. The RFID test equipment activates each RFID tag, acquires data, and reads the RFID tag including capturing the tag identification (ID) or serial number and capturing the status of a tamper bit included in the data emitted by the RFID tag. The RFID test equipment also sends a signal of the tag and tamper bit status to a central processing unit (CPU) or server 52 for storage and use in culling-out bad pads as indicated at informational block 54. The RFID test equipment may also send a signal to a high-speed inkjet printer for marking pads that either fail to be read or for which the tamper bit has not been properly set to indicate that the associated electrode trace forms a closed circuit.

In some embodiments, the criteria for determining a test failure by the RFID test equipment in connection with the first burst of energy are defined as follows: (1) failure to acquire and read the RFID tag serial number resulting in a "No Read" condition, or; (2) acquisition of the RFID tag serial number but failure to read and acquire the status of the tag tamper bit resulting in a "No Tamper Status" fault, or; (3) RFID tag tamper bit having a status of "0" (Open Circuit) status resulting in an "Open Circuit" fault. On the other hand, the criteria for determining a test acceptance by the RFID test equipment in connection with the first burst of energy to read the RFID tag is defined as follows: (1) acquiring the RFID tag serial number, and; (2) acquiring the tamper bit status, and (3) the RFID tag tamper bit having a status of "1" (Closed Circuit). So, if all three conditions for test acceptance are not received, the test is to be deemed a test failure and the pad under test is to be handled in the manner discussed below.

In some embodiments, in response to being energized with a burst of energy the second time by the RFID tag test equipment, each RFID tang is configured to respond by wirelessly sending an electronic product code (EPC). The criteria for determining a test failure of the tested RFID tag and the corresponding incontinence detection pad under test in connection with the second burst of energy are as follows: (1) if the EPC is not sent wirelessly from the tested RFID tag, or (2) if the EPC from the tested REIT) tag does not match a predetermined tag code. In one embodiment, the first RFID tag test takes about 45 milliseconds and the second RFID tag test takes about 40 milliseconds. In some embodiments, the EPC of the RFID tags is 40 characters in length and the same EPC is used and is common to all RFID tags. The energy emitted to read the RFID tag during the first and second tests is within a frequency compatible with the RFID tag design.

According to the present disclosure, the RFID test equipment of block 50 enters a "Ready for Operation" mode in response to sensing web movement and then goes into "Full Operation" mode when the 50 pads/minute (150 FPM) production rate occurs (or, in some embodiments, sooner if RFID tags are already loaded into position on the backsheet material 12 at lower speeds) and testing by the RFID test equipment ceases if the converting line 30 stops or if RFID tags fail to be placed onto the continuous web by the tag applicator at block 36. In some embodiments, the RFID test equipment detects a leading edge of the contrasting color airlaid core material 24 using a compact photoelectric sensor/eye mark detector. One suitable eye mark detector is the Omron E3Z photoelectric sensor available from Omron Corporation of Kyoto, Japan.

After leading edge detection of the airlaid core material 24 or by monitoring a distance traveled (e.g., 900 mm), the RFID test equipment, with an appropriate delay, is activated to read the RFID tag serial number, the status of the RFID tag tamper bit, and the EPC code of the RFID tag as described above. The REID test equipment relays a data packet of test result information from each individual test, along with the exact time of day the test was performed to server 52 which, in turn, communicates the data packet to the central PLC 39. The data is tabulated for long-term record storage and is also accessible to manual, offline RFID test equipment discussed below. The storage of test data in PLC 39 and/or server 52 and/or in some other server is indicated diagrammatically at block 55 which states "All Test Data Backed Up to Network Server for Future Access/Review."

In some embodiments, if one of the test failure conditions discussed above occurs, a reader of the REED test equipment at block 50 sends a signal with an appropriate delay as required to compensate for the speed of the converting line 30 to the ink jet print head which is located near an end of the RFID test station having the RFID test equipment and the print head prints one of the following marks conspicuously onto the backside of the backsheet material 12 at an appropriate location corresponding to the incontinence detection pad having the failed RFID tag: (1) an "N" is printed if a "No Read" condition occurs; (2) hyphen symbol, "-" is printed if no tamper bit is read; (3) a "0" is printed if the tamper bit is "0" indicating an "Open Circuit;" and (4) another code, such as an "E," is printed if the EPC cannot be read or is the wrong EPC. If desired, one code such as "E1" can be printed if the EPC cannot be read and another code such as "E2" can be printed if the wrong EPC is read from the RFID tag. A suitable printer for use in connection with block 50 includes the Keyence MK-U6000 series Universal Inkjet Printer available from Keyence Corporation of Osaka, Japan. In some embodiments of method 10, if ten RFID tags in arrow fail the RFID tag test, then server 52 sends a message to PLC 39 in this regard and PLC 39 shuts down the converting line 30 so that the root cause of the RFID tag test failures can be investigated and rectified.

In some embodiments, if the RFID test equipment fails to send a signal to the print head or to reject equipment including a product cull-out chute (discussed below) or if the print head goes offline, then the RFID test equipment updates its status to "Fault" and "Not Operating" modes and sends an output signal to the PLC 39 either directly or via server 52 in some embodiments, indicating the change in status. As shown in FIG. 1A, blocks 36, 48, and 50 of method 10 are sometimes collectively referred to as a Sealing Module of main converting line 30.

In the illustrative example, after the continuous web moves through the RFID test equipment of block 50, it passes by optional vision inspection equipment as indicated at block 56. Thus, in some embodiments, the vision inspection equipment of block 56 is omitted or is located elsewhere in the main converting line 30. If present, the vision inspection equipment may be made by Keyence Corporation of Osaka, Japan in some embodiments. The vision inspection equipment of block 56 includes a constant line screening camera and the acquired image data from the camera is processed to check for proper location of the continuous web on the converting line 30, proper electrode trace location on the continuous web, and proper RFID tag location on the continuous web. The vision inspection equipment of block 56 is programmed to know that the pad length of each incontinence detection pad is 900 mm which is about 36 inches. As indicated at informational block 58 of FIG. 1A, the vision inspection equipment of block 56 sends messages to PLC 39 to report and record vision defects for subsequent use in culling defective pads off of the converting line 30.

The vision inspection machine or equipment of block 56, which is downstream and independent of the RFID tag test equipment of block 50 in the illustrative example, determines an actual position of each registration mark of the series of registration marks on the backsheet material 12 as compared to a desired position of the registration marks. See the discussion above regarding the registration marks on backsheet material 12. The vision inspection machine of block 56 is able to see the registration marks through the backsheet material 12 of the continuous web and so operates as registration mark detector. An inspection signal is output from the registration mark detector of block 56 which indicates whether the second motor at block 34 should be operated to advance or retard the feed of the backsheet material 12 between the nip rollers. This is sometimes referred to as adjusting the "draught" of the backsheet material 12 through the nip rollers. In some embodiments, the second motor of the backsheet drive registration system 34 is advanced or retarded in increments of about $\frac{1}{8}$ inch. To be more specific, the inspection signal from the vision inspection machine of block 56 is provided to PLC 39 which, in turn, outputs a speed signal to feedback control the second motor of block 34. The speed signal from PLC 39 is also communicated to the RFID tag applicator of block 36 and to the RFID test equipment of block 50 to feedback control the RFID tang applicator and the RFID tag test equipment, respectively.

After the continuous web passes though the vision inspection equipment of block 56, the continuous web is folded in the machine direction as indicated at block 60 of FIG. 1A. As alluded to above, the machine direction is the direction parallel with the direction of movement of the continuous web through the converting line 30. In some embodiments, the continuous web has four machine direction folds introduced at block 60. See, for example, fold lines 252 in FIG. 9 (and the related discussion) of U.S. Patent Application Publication No. 2017/0246063 A1 which is already incorporated by reference herein. Blocks 56, 60 of method 10 are sometimes collectively referred to as a Longitudinal Folding Module of main converting line 30 as shown in FIG. 1A.

After the machine direction folds are made at block 60, the continuous web is cut to length as indicated at block 62. Block 62 is sometimes referred to as the Final Knife Module of method 10. Thus, at block 62, the continuous web is severed into the individual incontinence detection pads.

Block 62 is labeled as "Cut-to-Length (in Registration)." The term "in Registration" in block 62 is referring to the fact that a sacrificial trace portion of each electrode trace is severed and left behind on the next adjacent incontinence detection pad thereby resulting in first and second separate electrodes remaining on each cut-to-length incontinence detection pad. Spaced apart registration marks are provided on the sacrificial trace portion and on one of the electrode portions of each electrode trace to delineate a gap or space within which the final knife cut should be made. See, for example, the pair of registration marks 141a' in FIG. 25 (and the related discussion) of U.S. Patent Application Publication No. 2019/0060137, which is already incorporated by reference herein.

The final knife module of block 62 includes rollers through which the continuous web is fed prior to cutting. A shaft encoder is coupled to one of the rollers of the final knife module and has a shaft encoder that outputs 30 pulses per degree of revolution of the shaft, thereby to generate a speed signal that is communicated to PLC 39. PLC 39, in turn, provides the speed signal from block 62 to the equipment of blocks 34, 36, 50 so that, if needed, the operation of the equipment at blocks 34, 36, 50 is adjusted. After the continuous web is cut to length at the final knife module of block 62, the individual incontinence detection pads are folded in the cross direction as indicated at block 64. The cross-direction folds are substantially perpendicular to the machine direction folds and so, are made in the widthwise direction of the incontinence detection pads. In some embodiments, three cross direction folds are made at block 64. This involves folding the incontinence detection pads in half in the cross direction and then folding the incontinence detection pads in half again in the cross direction.

In some embodiments, as indicated at block 65, an open loop RFID test is performed after the incontinence detection pads are cut to length at block 62. In the illustrative example, the open loop RFID test of block 65 is shown after the cross direction folding operation of block 64 but the open loop RFID test can be performed prior to block 64 if desired. In the open loop RFID test, it is determined that the sacrificial trace has been cut properly from the electrodes under test and that an open circuit condition is properly communicated from the RFID tag along with the other data as discussed above in connection with the closed loop test of block 50. Thus, in some embodiments, the equipment used to perform the open loop RFID test at block 65 may include a Voyantic TAGSURANCE™ measurement system. If the tag is determined to be operating properly after testing at block 65, then this indicates that the RFID tag has been placed properly on the electrodes of the incontinence detection pad. Thus, testing at block 65 is one reason that the vision inspection at block 56 may not be needed, although embodiments within the scope of the present disclosure are contemplated in which vision inspection at block 56 and open loop RFID testing at block 65 are both present.

Referring now to FIG. 1B, after the cross direction folds are made to the incontinence detection pads at block 64, the incontinence detection pads that failed the vision inspection test of block 56 are culled out as indicated at block 66 and are recycled as indicated by dotted line arrow 68 and recycle icon 70. In some embodiments, a nozzle of pressurized air activates when an incontinence detection pad rejected at block 56 aligns with the nozzle. The pressurized air expelled from the nozzle propels the rejected pad onto a chute that angles downwardly and terminates above a recycle bin that collects the rejected pads for recycling. The direction at which the pressurized air from the nozzle is expelled is generally in the cross direction of converting line 30. In other embodiments, a mechanical system such as a push rod or tilting plate or bin is used to move rejected pads from the converting line 30 and onto the chute leading to the recycle bin at block 66. Blocks 64, 66 of method 10 are sometimes collectively referred to as a Bifolding Module of main converting line 30 as shown in FIGS. 1A and 1B.

After the pads having vision defects are culled from the converting line 30 at block 66, the pads that failed the closed loop RFID test at block 50 are culled out from the good pads as indicated at block 72 and collected in a bin, as indicated by dotted line arrow 74, for subsequent processing at an offline RFID test station as indicated at block 76. In some embodiments, the pads culled out at block 66 for vision defects are 11 pads away from the vision inspection equipment of block 56 and the pads culled out at block 72 for RFID test defects are 14 pads away from the RFID tag test equipment of block 50.

The offline RFID test at block 76 uses offline RFID tag test equipment that is basically similar to the equipment used at block 50 and/or at block 65, but may be operated manually by an operator in some embodiments. In other embodiments, the equipment at block 76 operates semi-automatically to load and test the pads. The offline RFID test at block 76 works in conjunction with the data obtained and tabled in server 52 by the the RFID tag test system of block 50 for read access and comparison of data so as to allow for quick determination by an engineer or any process operator should a culled pad's read status be requested or questioned. Accessing the previous test date from server 52 is indicated diagrammatically in FIG. 1B at block 78 which states "Query RFID Test Results."

In some embodiments, the offline RFID tag test system or equipment of block 76 includes a hand held or a fixed mounted RFID tag reader and a graphical user interface (GUI) that displays the initial test results from the test at block 50 as obtained from server 52 and the instantaneous test results being read at block 76. The purpose of operating the offline RFID tag test system of block 76 is to be able to recover pads that, for whatever reason, failed the RFID tag test of block 50 but that upon testing a second time, pass the RFID tag test. The offline RFID test system of block 76 is located on a portable work table located near converting line 30 or near an Optima pack line which is discussed below in further detail.

Upon presentation of a previously tested pad to the reader at the REID tag test station of block 76, if the pad's RFID tag is functional, the RFID tag test equipment activates and acquires the RFID chip within the passive REED tag of the pad being tested and obtains the RFID tag serial number. If RFID chip cannot be acquired or if obtaining the RFID tag serial is not possible, the pad is deemed defective and the GUI displays the test failure for the operator to read. The rejected pad is then recycled as indicated by dotted line arrow 80 and recycle icon 82 in FIG. 19.

The RFID tag test equipment of block 76 also reads the status of the RFID tag tamper bit. The tag tamper bit status should read "0" (Open Circuit status) at this point in the process, because after completion of the cut-to-length operation of block 62, the sacrificial trace portion of the electrode trace has been severed from the remaining portions of the electrode trace. If the tag status reads "1" (Closed Circuit status) at this point, the pad is deemed defective and the GUI displays the test failure for the Operator to read. The rejected pad is then recycled as indicated by arrow 80 and icon 82.

In some embodiments, a wire or other suitable conductor having alligator clips at its opposite ends or a bed of nails attached to a pneumatic cylinder test rig is attached to the two separate electrode trace portions of the pad near the outer edge of the pad where the electrode trace portions are not covered by the airlaid core laminate material 24. For examples of the electrode trace portions extending all the way to the outer edge of the incontinence detection pad, see FIGS. 31, 34A, 34B, 36, 39, 61A-62D, and 69F (and the related description) of U.S. Patent Application Publication No. 2018/0021184 A1; FIGS. 9 and 12A-13D (and the related description) of U.S. Patent Application Publication No. 2017/0246063 A1; and FIGS. 9A, 9C, 10, 11, 25 and 31A-31N (and the related description) of U.S. Patent Application Publication No. 2019/0060137, each of which is already incorporated by reference herein. Basically, the alligator clips and wire or bed of nails test rig serve as a proxy for the missing sacrificial trace portion. The teeth of the alligator clips or the nails of the bed of nails are able to puncture through the backsheet material 12 and/or the top sheet material 26 to make electrical contact with the electrode trace portions.

After the alligator clips and wire or bed of nails test rig are attached to the pad being tested, the RFID tag test equipment of block 76 is operated to read the status of the RFID tag tamper bit. The tag tamper bit status should read "1" (Closed Circuit status) at this point in the process because the alligator clips and wire, or associated conductor, are completing the electrode trace circuit. If the tag status reads "0" (Open Circuit status) at this point, the pad is deemed defective and the GUI displays the test failure for the Operator to read. The rejected pad is then recycled as indicated by arrow 80 and icon 82. If desired, the RFID tag test equipment at block 76 is operated to read the RFID tag tamper bit without the alligator clip and wire being attached to the pad under test and with the alligator clip and wire being attached to the pad under test. By running the test with and without the alligator clip and wire being attached to the pad, the proper operation of the RFID chip of the pad under both open circuit conditions (i.e., when no incontinence is on the pad) and closed circuit conditions (i.e., incontinence is on the pad and bridges the electrode trace portions) is reasonably assured when the pad is eventually used in a healthcare facility.

In some embodiments, once a pad under test at the offline RFID tang test station of block 76 is determined to be a rejected pad, the operator inspects the pad to verify that the printed markings (described above) on the pad match the defect that was detected during the offline RFID tag test of block 76. By confirming correspondence between the reason for rejection at block 50 and the reason for rejection at block 76, the proper operation of the RFID tag test equipment of blocks 50,76 is reasonably assured. If the reason for rejection at block 50 and block 76 do not match, then the operator may decide to inspect the test equipment to determine if there is a problem with the equipment that should be rectified. The reason for rejection of each of pads at block 76 is communicated to, and stored in, server 52 and is associated with the previous test results in some embodiments and also correlated with other information such as the manufacturing date of the pad. This allows for subsequent analysis and future investigation of the test data being accumulated during the tests at block 50 and block 76. Similar data is stored in server 52 for pads passing the manual RFID tag test at block 76.

In some embodiments, the RFID tang test equipment of block 76 includes an enclosure in which the pad under test is placed and then an operator steps on a foot pedal to cause an antenna in the enclosure to energize the RFID chip for reading. The rejection of pads at block 76 can occur in any of the ways described above in connection with block 50 (e.g., missing RFID tag or RFID tag cannot be acquired at all, EPC missing or not correct, or tamper bit not in proper state). If desired, the pad is removed from the enclosure, the alligator clips and wire are attached and then the pad is placed back in the enclosure for an additional tamper bit test.

The present disclosure also contemplates that a portion of the offline RFID tag test can be automated as indicated at block 84. In such an automated test, rejected incontinence detection pads are provided to the automated RFID test equipment at bock 84 as indicated by dotted arrow 86. In the automated RFID tag test at block 84, for example, the operator does not need to press the foot pedal each time a pad is to be read, but rather, the test equipment operates automatically to energize the RFID tag multiple times during the testing. Also, interconnecting the electrode trace portions of the test may be done with a semi-automated process instead of having to manually attach the alligator clips to the pad under test. For example, a pair of needles or prongs, or a pair of separate groups of needles or prongs (e.g., the bed of nails) may be controlled automatically to puncture through or at least into the incontinence detection pad while the pad remains folded, to electrically couple with the electrode trace portions near the boundary or outer edge of the incontinence detection pad. The tag status is then evaluated after the RFID chip is subsequently energized as described above. Pads rejected at block 84 are recycled as indicated by dotted line arrow 88 and icon 82. The data from the automated RFID tag test of block 84 is also compared with and associated with the data from the test of block 84 by server 52 as indicated by block 78.

Regardless of whether the incontinence detection pads are re-tested at block 76 or block 84, the pads that pass the offline RFID tag test are returned to a bagger 90 as indicated by dotted line arrow 92 of FIG. 1B. The incontinence detection pads that passed the first RFID tag test of block 50 are also provided to the bagger of block 90. As its name implies, 10 incontinence detection pads are placed in a bag at block 90. Blocks 72, 90 of method 10 are sometimes collectively referred to as a Packaging Module as shown in FIG. 1B and, in some embodiments, the equipment used at blocks 72, 90 is available from Optima Machinery Corporation of Green Bay, Wisconsin.

At block 94 a carton printer is operated to print relevant information on boxes that are to receive the bagged incontinence detection pads resulting from the bagging operation of block 90. At block 94, the boxes are in a generally flat or unfolded state. At block 96 a carton erector is operated to fold the boxes into their container-like form with a size and configuration suitable for receiving a particular number of bags from the bagger of block 90. Each bag has a particular number of incontinence detection pads therein. For example, if each bag has 10 incontinence detection pads therein and if four bags first into each carton, then each erected carton at block 96 receives 40 incontinence detection pads. Of course, this is just one arbitrary example and other sized bags and boxes may be used to hold more or less incontinence detection pads than the amounts given in the preceding example.

After the bags of incontinence detection pads are placed in the cartons erected at block 96, a unique device identification (UDI) label is placed on each of the cartons as indicated at block 98. UDI labels are required by the U.S. Food and Drug Administration (FDA) for medical devices and the information on the labels is specified by the FDA. For example, UDI labels are required to include a UDI which is established by an FDA-accredited issuing agency. In some embodiments of method 10, the labeling equipment of block 98 is provided by Label-Aire, Inc. of Fullerton, California.

After the UDI labels are applied to the cartons at block 98, the cartons are conveyed to a warehouse robotic palletizer as indicated at block 100. At block 100, the robotic palletizer places the cartons on pallets for subsequent handling. For example, a forklift 102 moves the completed pallets of cartons from block 100 to final goods (FG) inventory 104 for subsequent distribution to healthcare facilities or to other distribution facilities that, in turn, distribute the pallets, or a lesser number of cartons from the pallets, to healthcare facilities as indicated at block 106.

Figure 4:
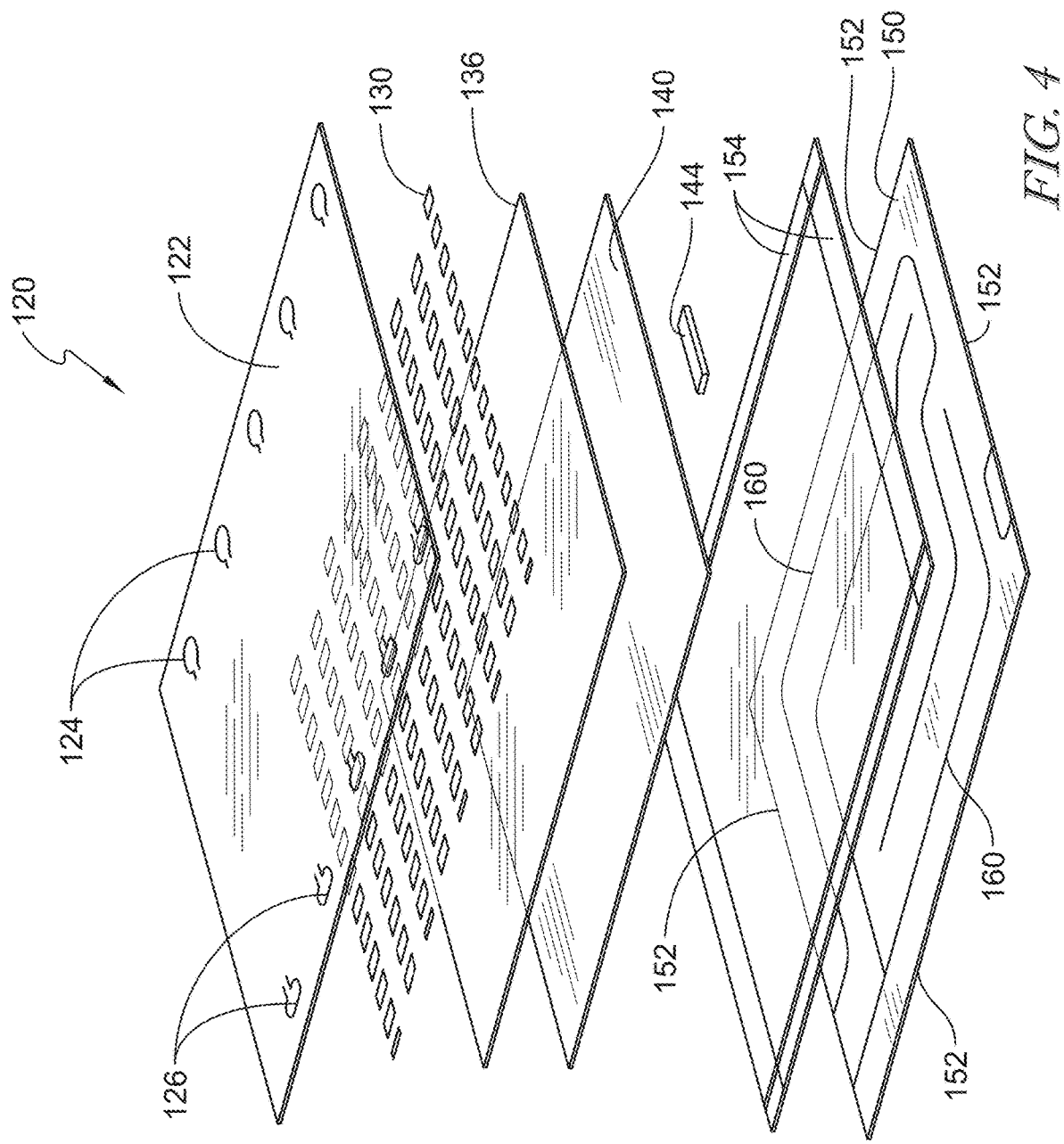
FIG. 4 is an exploded view of an incontinence detection pad formed with the jig of FIG. 2.

Referring now to FIG. 4, an incontinence detection pad 120 is formed using the methods and systems described above. The incontinence detection pad 120 is similar to the incontinence detection pads described in U.S. Patent Application Publication No. 2019/0060137, but uses a spaced checkerboard adhesive configuration in lieu of the slot coated adhesive layer 24 in the embodiments of FIGS. 1, 2, 23 and 24 of U.S. Patent Application Publication No. 2019/0060137. The spaced checkerboard adhesive configuration can also be used in a similar manner with the embodiment of FIG. 19 of U.S. Patent Application Publication No. 2019/0060137.

The pad 120 includes a top sheet 122 having head indicia 124 and foot indicia 126 printed thereon for orientation on a patient support apparatus (not shown). It should be noted that the head indicia 124 and the foot indicia 126 are optional and may not be printed on the top sheet 122. In some embodiments, the top sheet 122 is formed from a non-woven material.

A layer of adhesive 130 is positioned below the top sheet 122 in a spaced checkerboard configuration. In some embodiments, the layer of adhesive 130 is spray-coated onto a moisture absorbent core 136 to adhere the top sheet 122 to the moisture absorbent core 136. A low volume fluid filter layer 140 is positioned beneath the moisture absorbent core 136 in some embodiments, but is omitted in other embodiments. A radio frequency identification (RFDI) tag 144 is positioned beneath the fluid filter layer 140. In some embodiments, the RIFD tag 144 is a passive radio frequency identification tag 144. A backsheet material 150 is adhered to the top sheet 122 to secure the other layers between the backsheet material 150 and the top sheet 122. The backsheet material 150 is adhered to the top sheet 122 with peripheral hot melt adhesive 154 that is applied to the edges 152 of the backsheet material 150, i.e. applied to all four edges 152 of the backsheet material 150.

The backsheet material 150 is formed from a non-woven layer having a laminate of polyethylene, in some embodiments. An electrode trace 160 is printed on the backsheet material 150. In some embodiments, a plurality of electrode traces 160 are printed on the backsheet material 150. The electrode trace 160 is electrically coupled to the RFID tag 144.

FIG. 5 illustrates the adhesive layer 130 applied to the moisture absorbent core 136. The adhesive layer 130 includes a plurality of rows 170 of spaced apart adhesive marks 172. Each row 170 extends in a latitudinal direction 174 (aka the cross direction) and each adhesive mark 172 is spaced in the latitudinal direction 174 to form valleys 176 between each adhesive mark 172. The layer of adhesive 130 also includes a plurality of offset rows 180 of adhesive marks 182. Each offset row 180 is positioned between adjacent rows 170 and spaced from the rows 170 to form a channel 184 between each row 170 and the adjacent offset row 180. The offset rows 180 extend in the latitudinal direction 174 and each adhesive mark 182 is spaced in the latitudinal direction 174 to form valleys 186 between the adjacent adhesive marks 182.

The adhesive marks 182 of the offset rows 180 are offset from the adhesive marks 172 of the rows 170. That is, when moving in a longitudinal direction 190 (aka the machine direction) that is perpendicular to the latitudinal direction 174, each adhesive mark 182 is aligned with a valley 176 formed between adhesive marks 172. Likewise, each adhesive mark 172 is aligned in the longitudinal direction 190 with a valley 186 between adhesive marks 182. It should be noted that some of the adhesive marks 172 along the edges 192 of the top sheet 122 are partially applied to the moisture absorbent core 136 because of space constraints. Likewise, in some embodiments, the adhesive marks 182 may be partially applied along the edges 192 of the moisture absorbent core 136 depending on the spray-coating operation to apply the adhesive marks 172 and 182.

Referring to FIG. 6, the channels 184 between the rows 170 and the offset rows 180 extend a length of the moisture absorbent core 136. The channels 184 have a depth 200 that is defined from a top 206 of the adhesive marks 172 and 182 to a top surface 202 of the moisture absorbent core 136. The depth 200 of the channels 182 is substantially equivalent to a depth 204 of the valleys 186 (shown) and the valleys 176 (not shown). It will be appreciated that when the top sheet 122 is adhered to the moisture absorbent core 136, the adhesive marks 172 and 182 may flatten some and alter the depths 200 and 204. Nevertheless, after adhering the top sheet 122 to the moisture absorbent core 136, the adhesive marks 172 and 182 space the top sheet 122 and the moisture absorbent core 136 to maintain the channels 182 and the valleys 176 and 186.

Although certain illustrative embodiments have been described in detail above, variations and modifications exist within the scope and spirit of this disclosure as described and as defined in the following claims.

The invention claimed is:

1. A method of manufacturing incontinence detection pads that have wireless communication capability, the method comprising
    readying an RFID tag applicator to place RFID tags on backsheet material that is fed between a pair of nip rollers, the backsheet material having a series of electrode traces thereon;
    operating a nip roller motor to feed the backsheet material between the pair of nip rollers and toward the RFID tag applicator;
    operating the RFID tag applicator to place each RFID tag across regions of a respective electrode trace of the series of electrode traces; and
    operating RFID tag test equipment to energize each RFID tag a first time and a second time using wireless emissions and receiving return signals from each RFID tag in response to the wireless emissions, wherein in response to being energized the first time by the RFID tag test equipment, each RFID tag is configured to respond by sending first data wirelessly, wherein in response to being energized the second time by the RFID tag test equipment, each RFID tag is configured to respond by sending second data wirelessly, the second data being different than the first data.

2. The method of claim 1, wherein the first data includes at least a tag serial number and a tag status of an RFID chip of the RFID tag, and wherein the second data includes at least an electronic product code (EPC).

3. The method of claim 2, further comprising designating a tested RFID tag and the corresponding incontinence detection pad as a test failure if the tag serial number is not sent wirelessly from the tested RFID tag in response to the tested RFID tag being energized the first time.

4. The method of claim 2, further comprising designating a tested RFID tag and the corresponding incontinence detection pad as a test failure if tag status sent wirelessly from the tested RFID tag in response to the tested RFID tag being energized the first time indicates that the respective electrode trace forms an open circuit rather than a closed circuit.

5. The method of claim 2, further comprising designating a tested RFID tag and the corresponding incontinence detection pad as a test failure if the EPC is not sent wirelessly from the tested RFID tag or if the EPC from the tested RFID tag does not match a predetermined tag code, in response to the tested RFID tag being energized the second time.

6. The method of claim 2, further comprising, if a tested RFID tag and a corresponding incontinence detection pad are designated as a rejected incontinence detection pad due to a test failure by the RFID tag test equipment, removing the rejected incontinence detection pad from a packaging operation, and manually retesting the RFID tag of the rejected incontinence detection pad by using offline RFID tag test equipment.

7. The method of claim 6, further comprising, if the tested RFID tag is determined to be a twice-failing RFID tag due to still being a test failure after manual retesting, scrapping the rejected incontinence detection pad having the twice-failing RFID tag.

8. The method of claim 1, further comprising operating a registration mark detector independent of the RFID tag test equipment to determine an actual position of a registration mark of a series of registration marks on the backsheet material as compared to a desired position of the registration mark and outputting a signal from the registration mark detector that indicates whether a nip roller motor controller should be operated to advance or retard the feed of the backsheet material between the nip rollers.

9. The method of claim 8, further comprising providing the signal to a programmable logic controller (PLC) and outputting a speed signal from the PLC to feedback control the nip roller motor.

10. The method of claim 9, further comprising providing the speed signal from the PLC to the RFID tag applicator to feedback control the RFID tag applicator.

11. The method of claim 9, further comprising providing the speed signal from the PLC to the RFID tag test equipment to feedback control the RFID tag test equipment.

12. The method of claim 1, further comprising operating the RFID tag applicator to apply RFID tags to the backsheet material from a backing web that is initially in a packaged state and the RFID tag applicator unpackages the backing web.

13. The method of claim 12, further comprising operating a web removal machine to remove the backing web as the RFID tags are applied to the backsheet material by the RFID applicator.

14. The method of claim 13, wherein the web removal machine removes the backing web.

15. The method of claim 12, further comprising using a jig to manually splice a back end of one backing web with a front end of a next backing web.

16. The method of claim 1, further comprising adhesively marrying the backsheet material with a top sheet material and an absorbent core material prior to operating the RFID test equipment.

17. The method of claim 16, wherein adhesively marrying the backsheet material with the top sheet material and the absorbent core material involves a roll-marrying operation.

18. The method of claim 16, further comprising folding the adhesively married backsheet, top sheet, and absorbent core material in a machine direction, wherein the folding occurs downstream of the RFID tag test equipment.

19. The method of claim 18, further comprising cutting-to-length the folded backsheet, top sheet, and absorbent core material to create cut-to-length incontinence detection pads.

20. The method of claim 19, further comprising folding the cut-to-length incontinence detection pads in a cross direction to create ready-to-pack completed incontinence detection pads.

21. The method of claim 1, further comprising adhering a moisture absorbent core to a top sheet material with a layer of adhesive arranged in a spaced checkerboard configuration.

\* \* \* \* \*